(12) United States Patent (10) Patent No.: US 9,216,043 B2
Stad et al. (45) Date of Patent: Dec. 22, 2015

(54) DEVICES AND METHODS FOR MONOAXIAL SCREW CONVERSION

(71) Applicant: Medos International Sarl, Le Locle (CH)

(72) Inventors: Shawn D. Stad, Fall River, MA (US); Frank Spratt, Boston, MA (US); James Paiva, Warren, RI (US)

(73) Assignee: Medos International Sarl, Le Locle (CH)

( * ) Notice: Subject to any disclaimer, the term of this patent is extended or adjusted under 35 U.S.C. 154(b) by 82 days.

(21) Appl. No.: 13/831,430

(22) Filed: Mar. 14, 2013

(65) Prior Publication Data

US 2014/0277137 A1   Sep. 18, 2014

(51) Int. Cl.
*A61B 17/70* (2006.01)

(52) U.S. Cl.
CPC ........... *A61B 17/7076* (2013.01); *A61B 17/708* (2013.01); *A61B 17/7037* (2013.01); *A61B 17/7049* (2013.01); *A61B 17/7085* (2013.01); *A61B 17/7091* (2013.01)

(58) Field of Classification Search
CPC ........ A61B 17/7037; A61B 17/7074–17/7077; A61B 17/7083–17/7091
USPC .......... 606/86 A, 99, 104, 105, 266, 287, 290
See application file for complete search history.

(56) References Cited

U.S. PATENT DOCUMENTS

| | | | |
|---|---|---|---|
| 5,762,176 A | 6/1998 | Patterson et al. | |
| 6,648,888 B1 * | 11/2003 | Shluzas | 606/86 A |
| 6,736,820 B2 | 5/2004 | Biedermann et al. | |
| 6,974,460 B2 | 12/2005 | Carbone et al. | |
| 7,179,261 B2 | 2/2007 | Sicvol et al. | |
| 7,666,188 B2 | 2/2010 | Anderson et al. | |
| 7,842,044 B2 * | 11/2010 | Runco et al. | 606/104 |
| 7,918,857 B2 | 4/2011 | Dziedzic et al. | |
| 7,918,858 B2 | 4/2011 | Stad et al. | |
| 8,038,699 B2 * | 10/2011 | Cohen et al. | 606/246 |
| 8,197,484 B2 * | 6/2012 | Sato et al. | 606/86 B |
| 8,235,997 B2 * | 8/2012 | Hoffman et al. | 606/86 A |
| 8,328,817 B2 * | 12/2012 | Strauss | 606/102 |
| 8,398,683 B2 * | 3/2013 | Berrevoets et al. | 606/267 |
| 8,439,922 B1 * | 5/2013 | Arnold et al. | 606/86 A |
| 8,460,308 B2 * | 6/2013 | Marino et al. | 606/104 |
| 8,828,007 B2 * | 9/2014 | Stad et al. | 606/86 A |
| 8,894,662 B2 * | 11/2014 | Varieur et al. | 606/104 |

(Continued)

OTHER PUBLICATIONS

International Search Report for PCT/US14/021204 mailed Sep. 1, 2014 (7 pages).

*Primary Examiner* — Eduardo C. Robert
*Assistant Examiner* — Jacqueline Johanas
(74) *Attorney, Agent, or Firm* — Nutter McClennen & Fish LLP

(57) ABSTRACT

Devices and methods for selectively converting polyaxial bone screws into monoaxial screws are described herein. In one embodiment, a spinal screw extension instrument is provided having an outer component configured to engage a receiving member of a polyaxial screw. The instrument further includes an inner component disposed within an inner lumen of the outer component and configured to translate longitudinally relative to the outer component such that the inner component can apply a distal force to a compression member of the polyaxial screw disposed within a distal portion of the receiving member to thereby convert the polyaxial screw to a monoaxial screw.

16 Claims, 17 Drawing Sheets

(56) References Cited

U.S. PATENT DOCUMENTS

| | | |
|---|---|---|
| 2004/0147937 A1* | 7/2004 | Dunbar et al. .................. 606/99 |
| 2005/0131408 A1* | 6/2005 | Sicvol et al. .................... 606/61 |
| 2005/0149036 A1 | 7/2005 | Varieur et al. |
| 2005/0149048 A1* | 7/2005 | Leport et al. ................... 606/99 |
| 2006/0079909 A1* | 4/2006 | Runco et al. ................... 606/99 |
| 2008/0077135 A1 | 3/2008 | Stad et al. |
| 2009/0105770 A1* | 4/2009 | Berrevoets et al. ........... 606/308 |
| 2009/0143828 A1* | 6/2009 | Stad et al. .................. 606/86 A |
| 2009/0149887 A1* | 6/2009 | Schlaepfer et al. ........... 606/278 |
| 2009/0163956 A1* | 6/2009 | Biedermann et al. ......... 606/265 |
| 2009/0228054 A1* | 9/2009 | Hoffman et al. ............ 606/86 A |
| 2010/0114108 A1* | 5/2010 | Strauss ......................... 606/102 |
| 2010/0137875 A1* | 6/2010 | Marino et al. ................. 606/104 |
| 2010/0160977 A1* | 6/2010 | Gephart et al. ............... 606/305 |
| 2010/0262195 A1 | 10/2010 | Jackson |
| 2011/0034962 A1* | 2/2011 | Dunbar et al. ............. 606/86 A |
| 2011/0166606 A1 | 7/2011 | Stihl et al. |
| 2011/0257692 A1* | 10/2011 | Sandstrom et al. ......... 606/86 A |
| 2012/0215266 A1* | 8/2012 | Jones .......................... 606/86 A |
| 2013/0085536 A1* | 4/2013 | Biedermann et al. ......... 606/308 |
| 2014/0163625 A1* | 6/2014 | Meyer et al. ................ 606/86 A |
| 2014/0277137 A1* | 9/2014 | Stad et al. ..................... 606/246 |

* cited by examiner

DEVICES AND METHODS FOR MONOAXIAL SCREW CONVERSION

FIELD

The present invention relates to methods and devices for use in spinal surgery and, in particular, to instruments and methods for use during spinal fixation procedures.

BACKGROUND

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. Alternatively, two rods can be disposed on the lateral or anterior surface of the vertebral body in a substantially parallel relationship. The fixation rods can have a predetermined contour that has been designed according to the properties of the target implantation site and, once installed, the rods hold the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a receiving member having a U-shaped slot for seating the fixation rod. The receiving member can be monoaxial and thus fixed relative to the threaded shank, or it can be polyaxial and thus movable relative to the threaded shank. Polyaxial screws can facilitate positioning of the fixation rod therein. Extension instruments are often coupled to the receiving member, especially in minimally invasive procedures, to provide a pathway through tissue to the receiving member. A set screw, plug, or similar type of closure mechanism, is used to lock the fixation rod into the receiving member of the pedicle screw.

While current spinal fixation systems have proven effective, difficulties have been encountered in mounting rods into the receiving member of various fixation devices. In particular, it can be difficult to align and seat the rod into the receiving portion of adjacent fixation devices due to the positioning and rigidity of the vertebra into which the fixation device is mounted. While polyaxial pedicle screws can facilitate positioning of the fixation rod within the receiving member, additional correction of spinal deformities is often required. For example, the alignment of multiple vertebral levels can require manipulation of the extension instruments at each level to achieve the desired results. During these manipulation steps, the polyaxial screw is converted into a monoaxial screw to allow the surgeon to grasp the extension instrument and thereby manipulate the vertebra coupled thereto. While closure mechanisms can provide the ability to intraoperatively lock the polyaxial feature of the screw independent of locking the fixation rod within the receiving member, the closure mechanism can only be utilized after the rod is positioned within the receiving member, as it is inserted in a top-down fashion to press the rod into the U-shaped slot. In an open procedure, the rod can often be placed within the receiving member prior to correction, and thus conversion of the polyaxial screw into a monoaxial screw can often be achieved using the closure mechanism. In a minimally invasive deformity correction procedure, however, surgeons often utilize a "rod second" approach. This means that the spine is provisionally corrected prior to placing the rod within the receiving member. In a "rod second" approach the closure mechanism cannot be utilized to convert the polyaxial screw into a monoaxial screw.

Accordingly, there is a need for devices and methods for intraoperatively and selectively converting a polyaxial screw into a monoaxial screw to facilitate deformity correction and other operations during spinal surgery.

SUMMARY

The present invention generally provides devices and methods for intraoperatively and selectively converting a polyaxial screw into a monoaxial screw. Such devices and methods can be used, for example, during spinal surgery to aid surgeons in correcting deformities or otherwise manipulating a patient's vertebrae during an operation. The devices and methods described herein are designed for use with a variety of known polyaxial screw configurations. In some embodiments, the devices can include an outer component configured to couple with a receiving member of a polyaxial screw and an inner component configured to translate longitudinally with respect to the outer component. By translating the inner component distally while the outer component is coupled to a polyaxial screw, the distal end of the inner component can apply a distal force to a portion of the polyaxial screw and prevent polyaxial movement between the receiving member and a threaded shank of the bone screw. In such a configuration, the polyaxial screw is effectively converted into a monoaxial screw. The devices and methods described herein are particularly advantageous because the conversion between a polyaxial and a monoaxial screw is selective and reversible. This allows surgeons the freedom to either move or restrain the receiving member when desired, thereby permitting a single polyaxial screw to be used for a variety of procedures.

In one aspect, a spinal screw extension instrument is provided that includes an outer component having an inner lumen extending therethrough and a distal end with opposed arms configured to engage a receiving member of a polyaxial screw such that opposed slots formed between the opposed arms are aligned with opposed slots formed in the receiving member. The instrument further includes an inner component disposed within the inner lumen of the outer component and having a distal end with opposed arms and opposed slots formed between the opposed arms. The inner component can be configured to translate longitudinally relative to the outer component such that the opposed slots of the inner component are aligned with the opposed slots of the outer component and the receiving member. Further, the opposed arms of the inner component can be configured to apply a distal force to a compression member of the polyaxial screw disposed within a distal portion of the receiving member to thereby convert the polyaxial screw to a monoaxial screw.

The devices and methods described herein can include a number of additional features or variations, all of which are considered within the scope of the invention. For example, in some embodiments, the distal end of the inner component can extend distally beyond the distal end of the outer component when applying the distal force to the compression member of the polyaxial screw. Further, in some embodiments, the inner component can include a surface feature to prevent rotation relative to the outer component during longitudinal translation. Exemplary surface features can include a pin, setscrew, or other protrusion that extends from a surface of one component (e.g., from the outer surface of the inner component or the inner surface of the outer component) and interfaces with a slot or other recess formed on the other component.

In certain embodiments, a proximal portion of the inner component can be configured to threadably engage with the outer component such that rotation of the proximal portion of the inner component can translate the inner component relative to the outer component. In such an embodiment, the proximal portion of the inner component can be rotatably coupled to a distal portion of the inner component such that the distal portion of the inner component can be restrained from rotating with the proximal portion (e.g., using the surface feature and complementary recess described above). In some embodiments, the rotatable coupling can be accomplished by providing a circumferential groove or recess formed in one portion (e.g., the proximal or distal portion of the inner component) and a pin formed in the other portion that seats within the groove to hold the two portions together but allow relative rotation therebetween. As a result, the distal portion of the inner component can translate without rotating relative to the outer component when the proximal portion is rotated to effect the translation of the inner component.

In other embodiments, the instrument can include an actuator coupled to the outer component and the inner component. The actuator can be configured to effect the longitudinal translation of the inner component relative to the outer component. In some embodiments, the actuator can include a threaded outer surface configured to engage with a threaded surface of the inner lumen of the outer component. In other embodiments, however, the actuator can include an inner lumen having a threaded surface configured to engage with a threaded outer surface of the inner component. In still other embodiments, the actuator can include both a threaded outer surface and an inner lumen having a threaded surface, and the threads on the surface of the inner lumen can be opposite-handed of the threaded outer surface.

The outer and inner components can have a variety of shapes and mechanical configurations. In some embodiments, the outer component can include opposed portions coupled such that the opposed arms at the distal end of the outer component are biased toward one another. In certain embodiments, the instrument can also include a retaining ring coupled to one of the opposed portions and encircling both opposed portions. The retaining ring can provide support against torsional deformation and limit how close the opposed arms at the distal end of the outer component are allowed to come.

In still other embodiments, the outer component can include an outer sleeve configured to engage a feature formed on an outer surface of the receiving member of the polyaxial screw, as well as an inner sleeve disposed within the outer sleeve and configured to abut against an upper surface of the receiving member of the polyaxial screw. The two sleeves, working in tandem, can securely engage the receiving member of the polyaxial screw.

In another aspect, a spinal fixation kit is provided that includes a polyaxial screw and a screw extension instrument. The polyaxial screw can include a threaded shank having a head formed on a proximal end thereof and a receiving member having a spherical seat formed in a distal portion thereof for seating the head formed on the threaded shank. The receiving member can also include an aperture extending through a distal end thereof to allow the threaded shank to extend distally from the receiving member. The polyaxial screw can further include a compression member disposed within the receiving member and having a first position in which the receiving member is polyaxially movable relative to the threaded shank, and a second position in which the compression member engages the head formed on the threaded shank to lock the threaded shank in a fixed position relative to the receiving member and thereby convert the polyaxial screw into a monoaxial screw. The screw extension instrument can include an outer component with a distal end configured to engage the receiving member such that opposed slots formed in the distal end of the outer component align with opposed slots formed in the receiving member. The screw extension instrument can further include an inner component coupled to the outer component and configured to longitudinally translate relative to the outer component. The inner component can have a distal end with opposed slots that are aligned with the opposed slots of the outer component and the receiving member, and the inner component can be configured to advance distally to apply a distal force to the compression member to move the compression member from the first position to the second position. This movement can effectively convert the polyaxial screw into a monoaxial screw until such time as the distal force from the inner component is removed.

As with the device described above, several variations and additional features can be included in the kit. For example, in some embodiments the inner component can extend distally beyond the distal end of the outer component when the compression member of the polyaxial bone screw is in the second position.

As described above, in some embodiments a proximal portion of the inner component can be configured to threadably engage with the outer component such that rotation of the proximal portion of the inner component can translate the inner component relative to the outer component. In such an embodiment, the proximal portion of the inner component can be rotatably coupled to a distal portion of the inner component such that the distal portion of the inner component can be restrained from rotating with the proximal portion (e.g., using the surface feature and complementary recess described above). As a result, the distal portion of the inner component can translate without rotating relative to the outer component when the proximal portion is rotated.

In other embodiments, the screw extension instrument can include an actuator coupled to the outer component and the inner component. The actuator can be configured to effect the longitudinal translation of the inner component relative to the outer component. The actuator can, in some embodiments, include a threaded outer surface configured to engage with a threaded surface of the outer component. In other embodiments, the actuator can include a threaded inner lumen configured to engage with a threaded outer surface of the inner component. Still further, in certain embodiments the actuator can include both a threaded outer surface and an inner lumen with a threaded surface, and the threads of the inner lumen can be opposite-handed of the threaded outer surface.

The outer and inner components can have a variety of shapes and mechanical configurations. In some embodiments, for example, the outer component can include opposed portions coupled such that the distal ends of the opposed portions of the outer component are biased toward one another. In still other embodiments, the screw extension instrument can include a retaining ring coupled to one of the opposed portions of the outer component and encircling both of the opposed portions. The retaining ring can provide support against torsional deformation and limit how close the distal ends of the opposed portions of the outer component are allowed to come.

In another aspect, a method for correcting spinal deformities is provided that includes coupling a screw extension instrument to a receiving member of a polyaxial screw, where the receiving member is coupled to a threaded shank that is polyaxially movable relative to the receiving member. The method can further include advancing an inner component of the screw extension instrument relative to the receiving member of the polyaxial screw to cause the inner component to convert the polyaxial screw into a monoaxial screw.

In certain embodiments, advancing the inner component of the screw extension instrument can include pushing a compression member disposed within a distal portion of the receiving member of the polyaxial screw onto a head formed on the threaded shank of the polyaxial screw to thereby prevent movement of the head relative to the receiving member. Once movement of the head relative to the receiving member is restricted, the polyaxial bone screw is effectively converted into a monoaxial bone screw.

In some embodiments, the method can further include implanting the threaded shank of the polyaxial screw in a vertebra before coupling the screw extension instrument to the receiving member of the polyaxial screw. However, in other embodiments, the order can be reversed and the method can include implanting the threaded shank of the polyaxial screw in a vertebra after coupling the screw extension instrument to the receiving member of the polyaxial screw.

In certain embodiments, the method can further include passing a spinal fixation rod through the receiving member of the polyaxial screw after advancing the inner component of the screw extension instrument to convert the polyaxial screw into a monoaxial screw. For example, in certain "rod second" approaches to spinal deformity correction, a surgeon will provisionally correct the position of a vertebra before inserting a rod. In order to be able to manipulate the vertebra, the surgeon can convert the polyaxial screw into a monoaxial screw, perform the provisional correction, and then pass the spinal fixation rod through the receiving member.

In some embodiments, it can be desirable to convert the monoaxial screw back into a polyaxial screw after, for example, provisionally correcting the position of a vertebra. This is because the polyaxial movement of the receiving head can make it easier to capture the spinal fixation rod. As a result, the method can, in some embodiments, include retracting the inner component of the screw extension instrument relative to the receiving member to convert the monoaxial screw into a polyaxial screw after advancing the inner component of the screw extension instrument.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention is generally directed to devices and methods for intraoperatively and selectively converting a polyaxial bone screw into a monoaxial bone screw. Such devices and methods can be used, for example, during spinal surgery to aid surgeons in correcting deformities or otherwise manipulating a patient's vertebrae during an operation. The devices and methods described herein are designed for use with a variety of known polyaxial screw configurations. The devices described herein generally include an outer component configured to couple with a receiving member of a polyaxial screw and an inner component configured to translate longitudinally with respect to the outer component and receiving member. By translating the inner component distally while the outer component is coupled to a polyaxial screw, the distal end of the inner component can apply a distal force to a portion of the polyaxial screw and prevent polyaxial movement between a receiving member and a threaded shank of the screw. In such a configuration, the polyaxial screw is effectively converted into a monoaxial screw. The devices and methods described herein can be particularly advantageous because the conversion between a polyaxial and a monoaxial screw is selective and reversible. This allows surgeons the freedom to either move or restrain the receiving member when desired, thereby permitting a single polyaxial screw to be used for a variety of procedures. Furthermore, the devices described herein are able to provide this selective conversion between polyaxial and monoaxial configurations without preventing the passage of a spinal fixation element through the receiving member of the screw.

Figure 1:
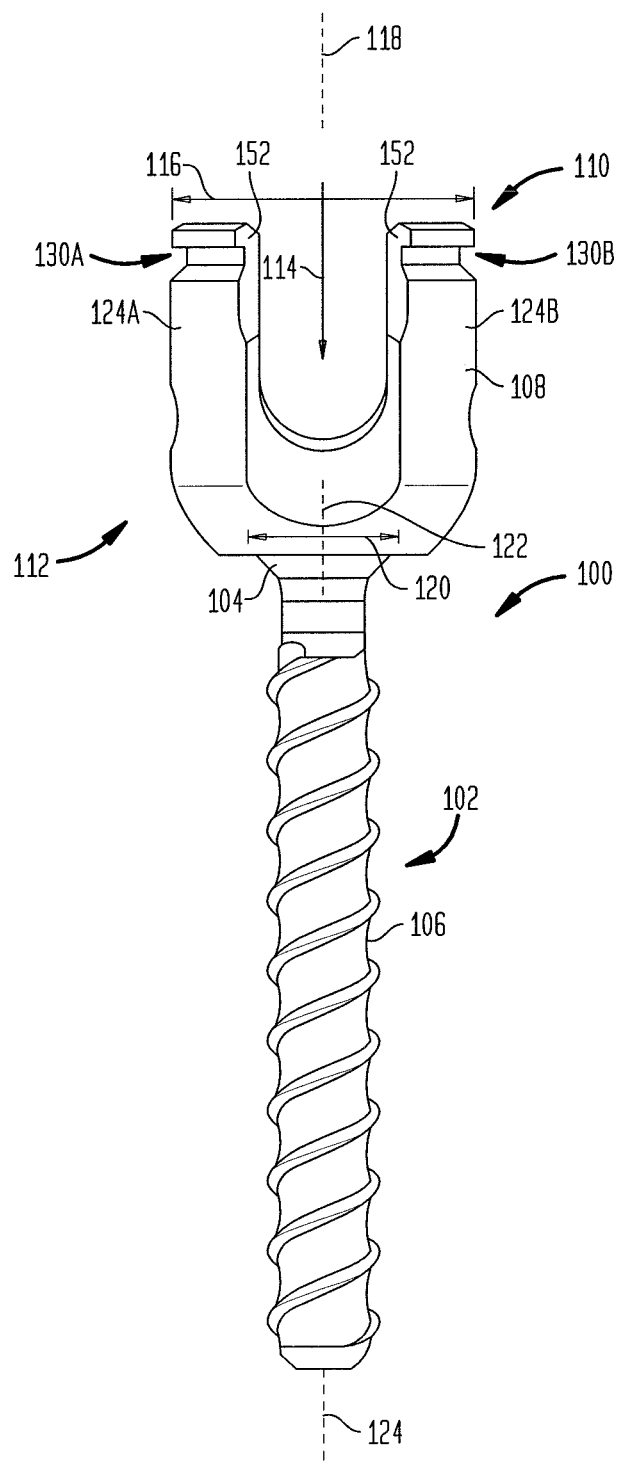
FIG. 1 is a front view of a prior art polyaxial screw.

FIG. 1 illustrates one embodiment of a polyaxial screw 100 known in the art. The polyaxial screw 100 includes a bone anchor 102, such as a pedicle screw, having a proximal head 104 and a distal bone-engaging portion 106, which in the illustrated exemplary embodiment is an externally threaded screw shank. The polyaxial screw 100 also includes a receiving member 108 that is configured to receive and couple a spinal fixation element, such as a spinal rod or spinal plate, to the polyaxial screw 100.

The receiving member 108 may be coupled to the bone anchor 102 in any manner known in the art. For example, the bone anchor 102 may be adjustable to multiple angles relative to the receiving member 108. This is in contrast to monoaxial bone screws, in which the bone anchor 102 and the receiving member 108 are not movable relative to one another. An exemplary polyaxial bone screw is described U.S. Pat. No. 5,672,176, which is herein incorporated by reference in its entirety.

The receiving member 108 of the illustrated exemplary embodiment includes a proximal end 110, a distal end 112, and a recess or slot 114 for receiving a spinal fixation element, such as a spinal rod. The proximal end 110 of the receiving member 108 has a first bore 116 formed therein that defines a first bore axis 118 and communicates with the recess 114 such that a spinal fixation element may be positioned through the first bore into the recess 114. The distal end 112 has a second bore 120 opposite the first bore 116 that defines a second bore axis 122 and is designed to receive the head 104 of the bone anchor 102 to couple the bone anchor to the receiving member 108. In the illustrated exemplary embodiment, the head 104 is seated within the second bore 120. As the exemplary illustrated embodiment of the bone anchor assembly is polyaxial, the bone anchor 102 is free to rotate relative to the receiving member 108 such that the longitudinal axis 124 of the bone anchor 102 is positionable at an angle relative to the second bore axis 122 of the receiving member 108 (in FIG. 1, the first bore axis 118, second bore axis 122, and longitudinal axis 124 of the bone anchor 102 are coaxial). The second bore 120 may be spherically or conically shaped to facilitate adjustment of the bone anchor 102 relative to the receiving member 108. In the exemplary embodiment, the receiving member 108 has a generally U-shaped cross-section defined by two legs 124A and 124B separated by recess 114. Each leg 124A, 124B is free at the proximal end 110 of the receiving member 108.

The receiving member 108 may be configured to receive a closure mechanism that locks a spinal fixation element within the recess 114. The closure mechanism may be a cap that is advanceable through the first bore 116 of the receiving member 108 and seats against the spinal fixation element. For example, the cap may have external threads that engage internal threads provided in the receiving member 108, e.g., on the legs 124A, 124B. Any type of conventional closure mechanism may be employed, including, for example, non-threaded caps, multi-component closure mechanisms, and/or external caps.

The receiving member 108 of the exemplary polyaxial screw 100 can include features allowing it to be releasably connected to an instrument, such as the screw extension instrument described below. For example, the receiving member 108 may include at least one groove 130 that is configured to receive a portion of an instrument to releasably connect the instrument to the polyaxial screw. The size, shape, position, and number of grooves can be varied depending on, for example, the instrument employed and the type of connection desired. In certain embodiments, for example, at least one arcuate groove 130 may be provided on an exterior surface of the proximal end 110 of the receiving member 108. In other exemplary embodiments, at least one arcuate groove may be provided on an interior surface of the proximal end 110 of the receiving member 108. In the illustrated exemplary embodiment, each leg 124A and 124B may be provided with an arcuate groove 130A, 130B, respectively, at the free, proximal end of the leg 124A, 124B. The grooves 130A, 130B may extend about a portion or the entirety of the circumference of the proximal end of each leg 124A, 124B. Each groove 130A, 130B may have a size and shape that is complementary in size and shape to a projection or other feature provided on the instrument, as described in more detail below.

Figure 2:
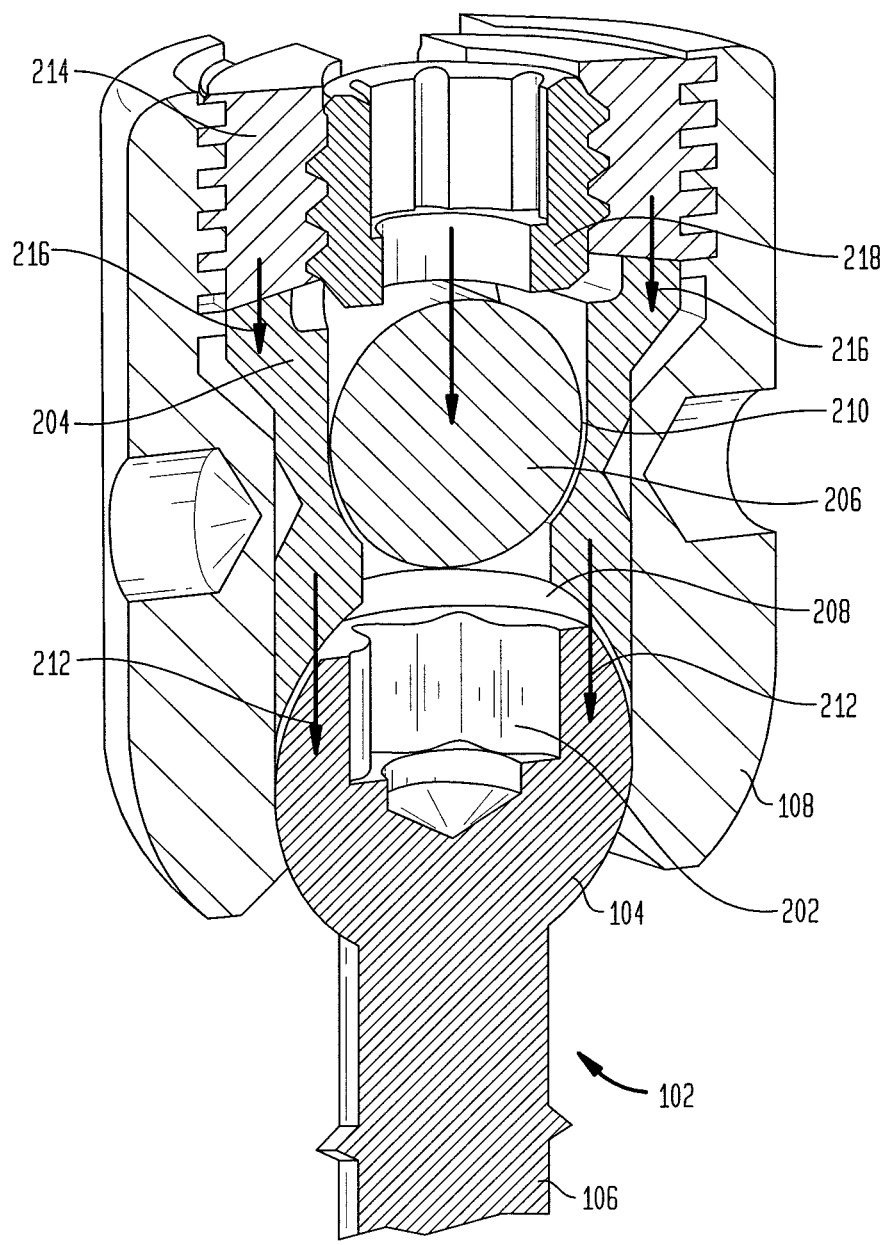
FIG. 2 is a front cross-sectional view of the prior art polyaxial screw of FIG. 1.

FIG. 2 illustrates the polyaxial screw 100 in cross-section. In particular, the spherical head 104 of the bone anchor 102 is shown extending through the second bore 120 formed in the distal end of the receiving member 108 and seated within a spherical seat in the receiving member. The head 104 can include a recess 202 or other feature that can receive a driver or other instrument that can be used to implant the bone anchor 102 in a vertebra. Also shown is a compression member 204 that resides within the recess 114 of the receiving member 108. The compression member 204 can include an inner lumen that allows a driver or other instrument to access the recess 202 of the bone anchor 102. Furthermore, the compression member 204 can include features formed at its proximal and distal ends that are configured to interface with a spinal fixation element, such as the spinal fixation rod 206, and the head 104 of the bone anchor 102, respectively. For example, the compression member 204 can include a hemispherical recess 208 formed at its distal end that can mirror the shape of the head 104 of the bone anchor 102. At its proximal end, the compression member 204 can include a U-shaped recess 210 that is configured to seat a spinal fixation element, such as the spinal fixation rod 206.

The compression member 204 can be configured to travel within the recess 114 of the receiving member 108 along the first bore axis 118 between a first position in which the compression member allows polyaxial movement of the head 104 within the receiving member 108 and a second position (shown by arrows 212 in FIG. 2) in which the compression member locks the orientation of the bone anchor 102 with respect to the receiving member 108. This is typically accomplished with the use of a closure mechanism, such as the outer set screw 214. As the outer set screw 214 is threaded into the proximal end of the receiving member 108, it can exert a downward force on the compression member 204 (shown by arrows 216 in FIG. 2), thereby pushing the compression member 204 from the first position to the second position and locking the orientation of the bone anchor 102 and the receiving member. The outer set screw 214 can itself include an inner lumen to receive an inner set screw 218 that can be used to lock the receiving member in a particular orientation and position along the spinal fixation rod 206 by pressing the rod into the U-shaped recess 210 of the compression member (shown by arrows 216 in FIG. 2).

Figure 3:
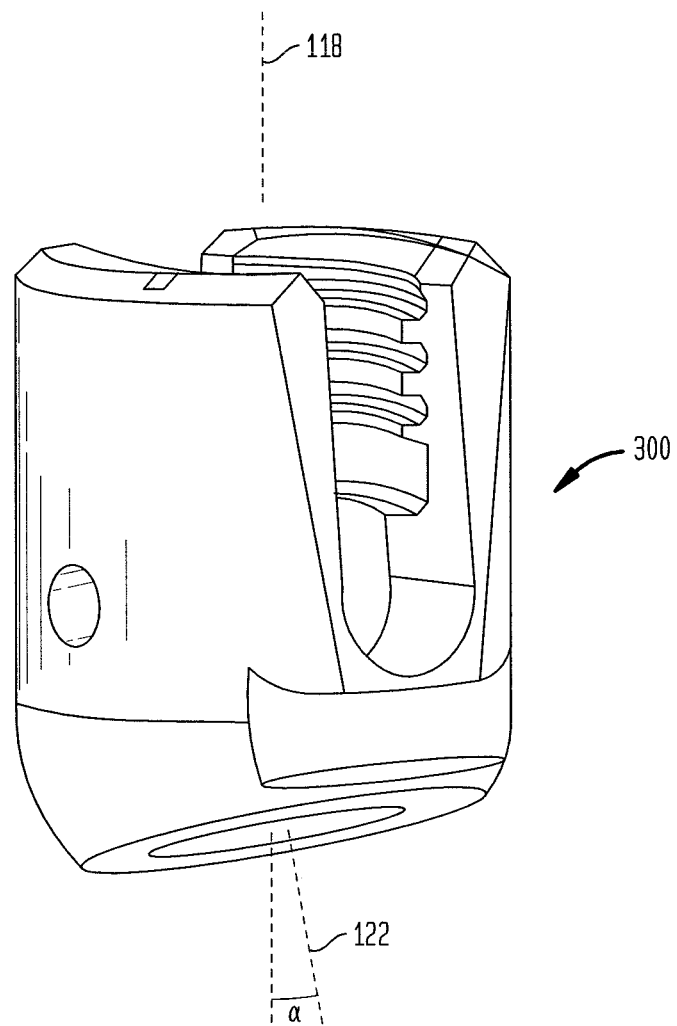
FIG. 3 is a perspective view of an alternative embodiment of a prior art receiving member of a polyaxial screw.

There are a number of variations on the polyaxial screw 100 known in the art. For example, FIG. 3 illustrates an embodiment of a polyaxial screw receiving member 300 that is biased to a particular angle or range of angles to provide a favored angle to the bone anchor 102. This favored angle can aid in rod capture during a spinal procedure as the receiving member 108 can have additional range of motion in one direction, e.g., laterally away from the spinal column. In favored angle embodiments, the second bore axis 122 can be positioned at an angle α (other than 0°) to the first bore axis 118. Exemplary favored angle bone screws are described in U.S. Pat. No. 6,736,820 and U.S. Pat. No. 6,974,460, both of which are herein incorporated by reference in their entirety.

Figure 4:
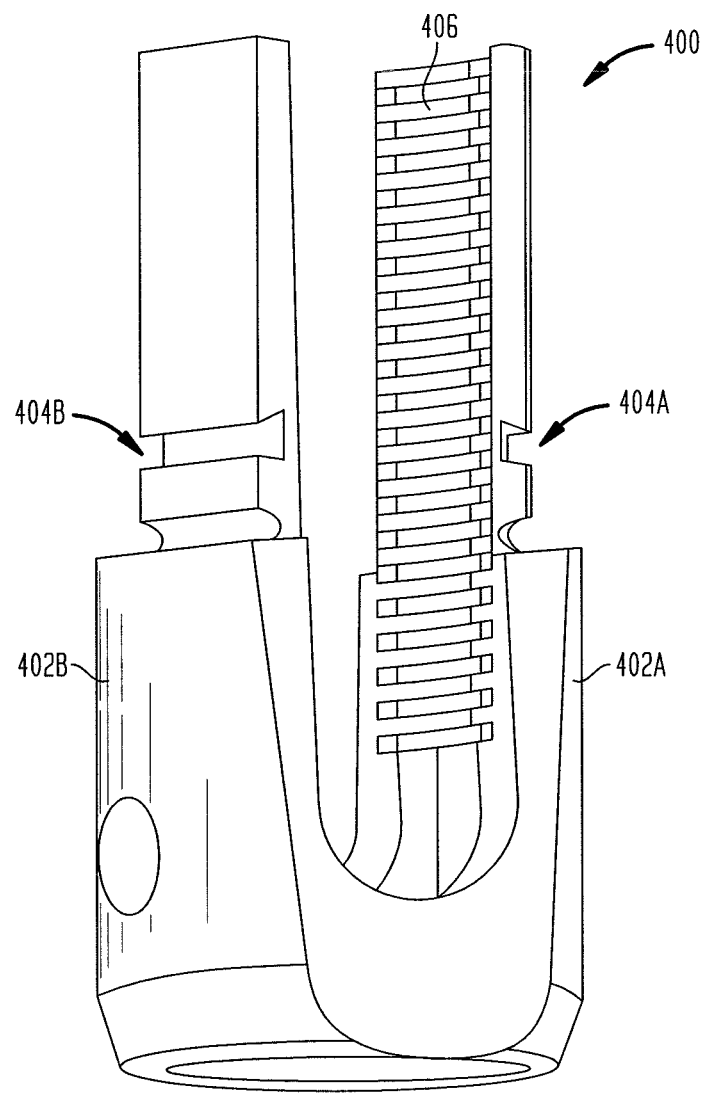
FIG. 4 is a perspective view of another alternative embodiment of a prior art receiving member of a polyaxial screw.

In other embodiments, polyaxial screws can include features to extend the legs 124A, 124B, as shown in FIG. 4. In the illustrated embodiment, the opposed legs 402A, 402B of the receiving member 400 each include tabs 404A, 404B extending from a proximal end of the receiving member 400. The tabs 404A, 404B can have a generally arcuate shape and can be configured to allow an instrument to releasably engage with the receiving member 400. The tabs 404A, 404B can include a feature or features for facilitating releasable engagement by an instrument. For example, the tabs can be provided with external threads, or can include one or more grooves. In the illustrated exemplary embodiment, each tab 402A, 402B includes one or more arcuate grooves 404A, 404B that may be analogous in construction to the grooves 130A, 130B described above. The tabs 402A, 402B can also include internal threads 406 to facilitate advancement of a closure mechanism, such as the outer set screw 214 discussed above, to the receiving member 400. Tabs 404A, 404B can be sheared off the receiving member 400 after a closure mechanism is applied to secure the position of the receiving member 400 and/or a spinal fixation element extending therethrough.

Surgical procedures to correct deformities or other abnormalities of the spine using the polyaxial screws described above typically involve implanting one or more polyaxial screws in the vertebrae that are to be adjusted, and using a spinal fixation element spanning across the polyaxial screws to impart and maintain a desired shape in the spine. Methods for performing these procedures typically involve implanting a plurality of polyaxial screws, capturing a spinal fixation element within the receiving members of the polyaxial screws, and then applying a closure mechanism, such as the outer and inner set screws described above, to lock the fixation element within the receiving members of the polyaxial screws. The polyaxial screws described above can be particularly advantageous because the independent functionality of the outer and inner set screws can allow the polyaxial screw to be intraoperatively converted into a monoaxial screw. Converting a polyaxial screw to a monoaxial screw intraoperatively can allow for more effective adjustment of the position and/or orientation of a given vertebra as forces are applied to the screw.

In certain procedures, however, surgeons adopt a "rod second" approach, in which the spine is provisionally corrected prior capturing a rod or other spinal fixation element within the receiving members of the implanted bone screws. This is especially popular in minimally invasive surgical (MIS) procedures, where the patient's spine is not wholly exposed during the operation and provisional correction of the spine's shape can facilitate easier percutaneous introduction of a spinal fixation rod or other element. To date, it has been impossible to leverage the advantages of the polyaxial screws described above because the requirement of a set screw to facilitate the conversion makes it impossible to pass a rod into the receiving member.

The present invention provides devices and methods that allow for the intraoperative and selective conversion of a polyaxial screw into a monoaxial screw while maintaining the ability to introduce a spinal fixation element into a receiving member of the screw. The devices and methods described herein can allow a surgeon or other user to convert a screw between polyaxial and monoaxial configurations as desired throughout a procedure (e.g., a polyaxial configuration can be preferred during rod capture and a monoaxial configuration can be preferred during derotation, fracture closure, and parallel compression or distraction procedures). This provides a surgeon or other user with increased flexibility to address anticipated or unforeseen difficulties that often occur during technically challenging spinal operations.

Figure 5:
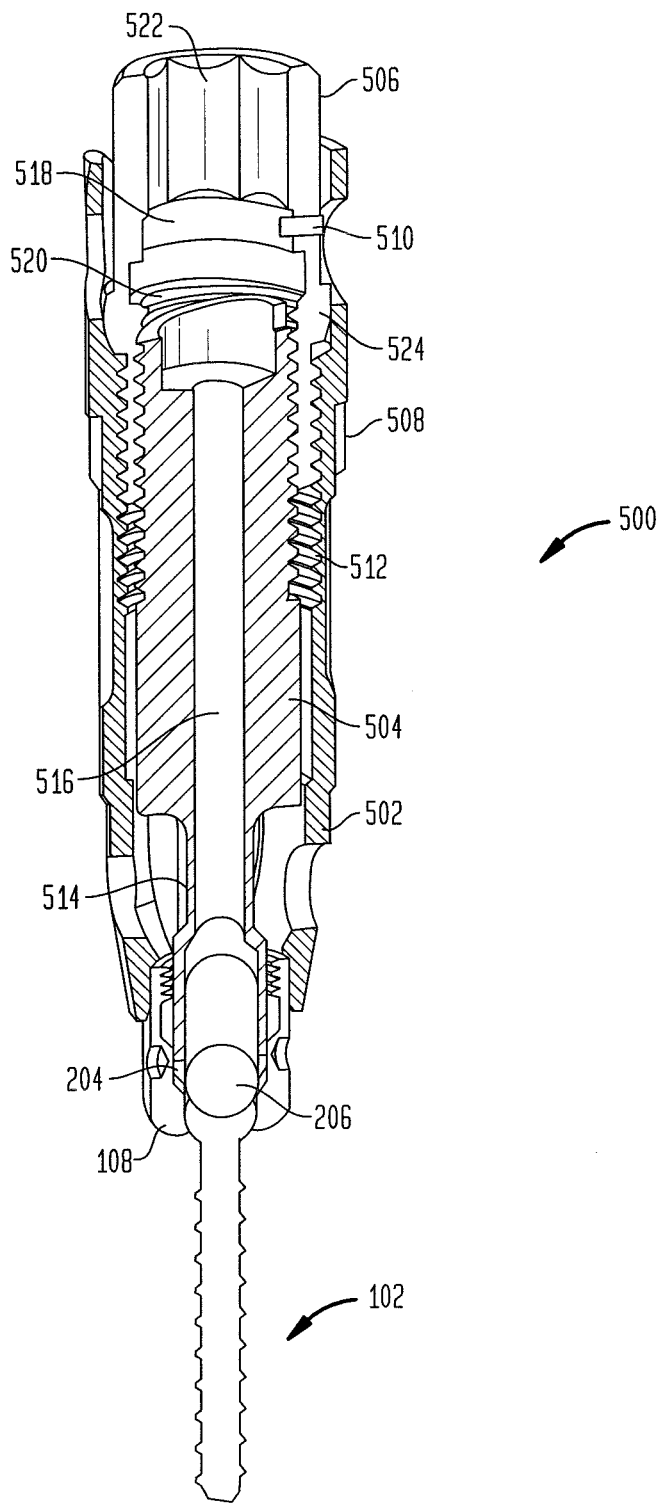
FIG. 5 is a perspective cross-sectional view of one embodiment of a screw extension instrument.

FIG. 5 illustrates one embodiment of a screw extension instrument 500 according to the teachings of the present invention. The screw extension instrument 500 is shown attached to the polyaxial screw 100 and having a spinal fixation rod 206 seated therein. As described above, the polyaxial screw 100 includes a bone anchor 102 coupled to a receiving member 108. The receiving member 108 includes a compression member 204 disposed within a distal portion of the receiving member and configured to move between a first position in which the bone anchor 102 can move polyaxially with respect to the receiving member, and a second position in which the bone anchor and the receiving member have a fixed orientation.

The screw extension instrument 500 can include an outer component 502, an inner component 504, and an actuator 506 coupled to the outer component and the inner component. The outer component 502 can have opposed arms configured to releasably engage with the receiving member 108 of the polyaxial screw 100 using, for example, features similar to the groove 130 described above. The inner component 504, which is disposed within an inner lumen of the outer component 502, can be configured to translate along the first bore axis 118 toward the compression member 204 disposed in the distal end of the receiving member 108. The inner component 504 can include opposed arms at a distal end thereof that are configured to apply a distal force to the compression member 204, thereby converting the polyaxial screw 100 into a monoaxial screw, as described above. The translation of the inner component 504 relative to the outer component 502 and the receiving member 108 can be effected by the actuator 506, at least a part of which can be positioned at a proximal end of the instrument 500 for ease of access. In addition, the alignment of the slots formed between the opposed arms of the outer component and the inner component with the U-shaped cross-section of the receiving member 108 allows for the introduction of the spinal fixation rod 206 even when the polyaxial screw is locked in a monoaxial configuration by the instrument 500.

Figure 6:
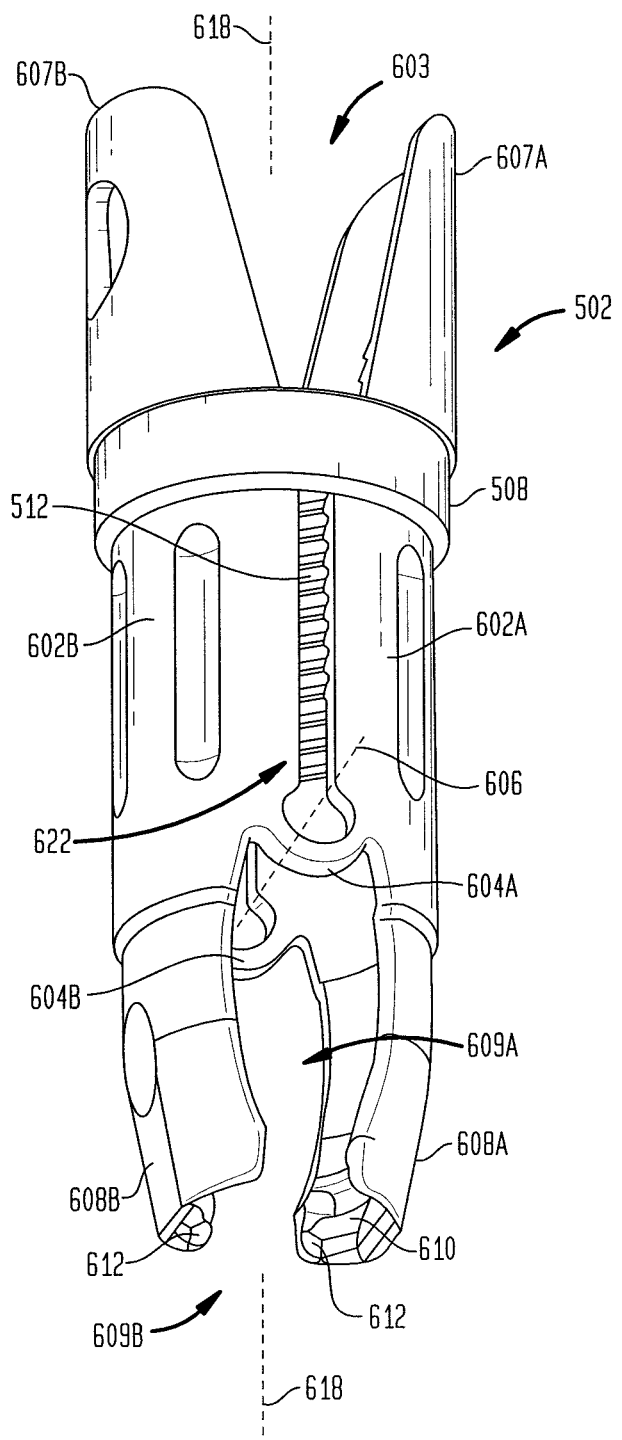
FIG. 6 is a perspective view of an outer component of the screw extension instrument of FIG. 5.

FIG. 6 illustrates one embodiment of the outer component 502 of the instrument 500. The outer component 502 can have a variety of shapes and sizes. In the illustrated embodiment, the outer component 502 has a generally cylindrical shape and is formed from two opposed portions 602A, 602B that define an inner lumen 603 extending therebetween. The opposed portions can include opposed arms 608A, 608B formed at a distal end of the outer component, and opposed tabs 607A, 607B formed at a proximal end of the outer component. The opposed portions can be coupled together by connecting portions 604A, 604B that define a pivoting axis 606 around which the opposed portions rotate toward or away from one another. Further, the connecting portions 604A, 604B can be formed such that the opposed portions 602A, 602B of the outer component 502 are biased toward or away from each other at the proximal and distal ends of the outer component. For example, in the illustrated embodiment, opposed arms 608A, 608B formed at the distal end of the opposed portions 602A, 602B can be biased toward one another and, correspondingly, the tabs 607A, 607B formed at the proximal ends of the opposed portions 602A, 602B can be biased away from one another. As a result, the outer component 502 can function similarly to a clothespin when releasably engaging with the receiving member 108 of the polyaxial screw 100.

The opposed arms 608A, 608B at the distal end of the outer component 502 can have a variety of shapes and sizes as well. In some embodiments, the opposed arms 608A, 608B can have a generally arcuate shape in cross-section and can define opposed slots 609A, 609B extending between the arms. The opposed arms can, in some embodiments, include features designed to facilitate engagement with the receiving member 108. For example, the inner surface of each arm can include a protrusion or recess configured to interface with a complementary feature formed on an outer surface of the receiving member 108. For example, in the illustrated embodiment, the inner surface of the opposed arms 608A, 608B can include a protrusion 610 configured to interface with the groove 130 of the receiving member 108. In addition, the outside edges of the opposed arms 608A, 608B can include contact surfaces 612 configured to abut against contact surfaces 152 (see FIG. 1) of the receiving member legs 124A, 124B. The contact surfaces 612 are similar to the finger-like extensions 82 described below (see FIG. 10) and can prevent the rotation of the receiving member 108 with respect to the outer component 502.

To releasably engage the outer component with the receiving member 108 of the polyaxial screw 100, a user can pinch the tabs 607A, 607B at the proximal end of the outer component 502 together using their hand or a tool. This action pivots the opposed portions 602A, 602B around the pivoting axis 606 and separates the opposed arms 608A, 608B at the distal end of the outer component. The receiving member 108 can then be advanced into the inner lumen 603 of the outer component between the opposed arms 608A, 608B. The tabs 607A, 607B can be released and the bias imparted by the connecting portions 604A, 604B can clamp the opposed arms 608A, 608B onto the receiving member 108 such that the receiving member and the outer component are securely coupled together.

The outer component 502 can also include a retaining ring 508 (also visible in cross section in FIG. 5) coupled thereto at a location proximal to the pivoting axis 606. The retaining ring can be sized such that it encircles the opposed portions 602A, 602B without excess clearance at a desired maximum separation between the opposed portions. The retaining ring 508 can provide resistance to shear forces acting along the pivoting axis 606. The retaining ring 508 can be coupled to one of the opposed portions 602A, 602B and can remain unattached to the other such that the retaining ring does not interfere with the ability of the opposed portions to pivot relative to one another to bring the opposed tabs 607A, 607B closer together. This can be accomplished, for example, by welding, mechanically fastening, or chemically adhering the retaining ring to one of opposed portion 602A or 602B.

Still further, the outer component 502 can include features to facilitate the longitudinal translation of the inner component with respect thereto. For example, an inner surface of the outer component (i.e., a surface of the inner lumen 603) can include threads 512 (also visible in cross-section in FIG. 5) to accept the actuator 506 that effects the translation of the inner component with respect to the outer component. Furthermore, opposing slots 622 (only one is visible in FIG. 6) can extend from the connecting portions 604A, 604B to the proximal end of the outer component and can be configured to accept a protrusion 710 (see FIG. 7) formed on an outer surface of the inner component 504 to prevent the inner component from rotating during translation.

Figure 7:
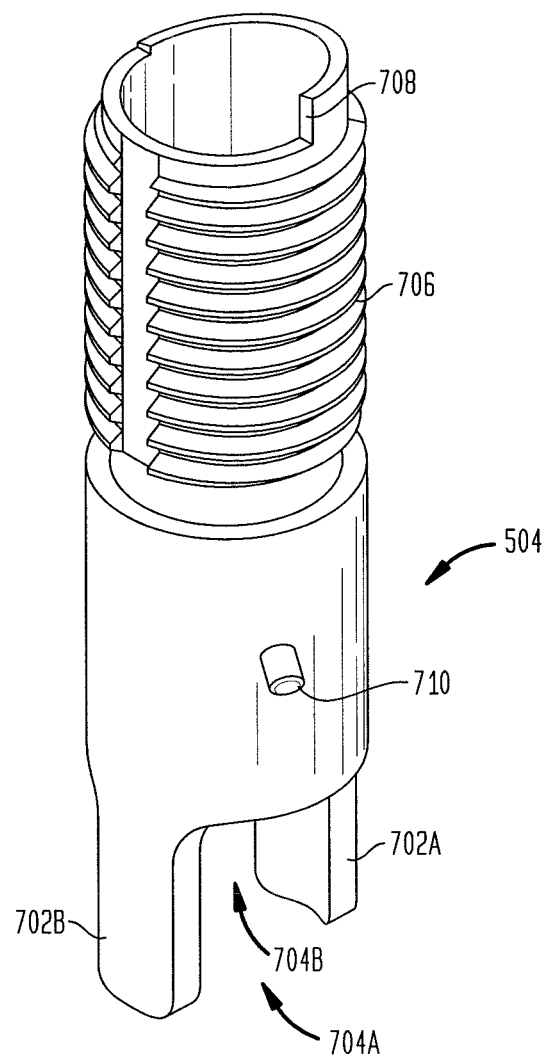
FIG. 7 is a perspective view of an inner component of the screw extension instrument of FIG. 5.

FIG. 7 illustrates one embodiment of the inner component 504 of the screw extension instrument 500. The inner component can have a variety of shapes and sizes but, in some embodiments, is a generally cylindrical body having opposed arms 702A, 702B formed at a distal end thereof with opposed slots 704A, 704B formed between the opposed arms. The arms can have a variety of shapes and sizes themselves, but in some embodiments are sized such that they can extend into the recess 114 of the receiving member 108 without interfering with the passage of a spinal fixation element, such as rod 206. In addition, the distal faces of the opposed arms 702A, 702B can have a shape, such as a planar surface, configured to interface with an upper surface of the compression member 204, thereby allowing the opposed arms to effectively impart a distal force onto the compression member.

The proximal end of the inner component can include a threaded outer surface 706 configured to threadably mate with the actuator 506. The threads formed on the outer surface of the inner component 504 can be opposite-handed from the threads formed on the inner lumen 603 of the outer component 502 (e.g., the threads formed on the outer component 502 can be right-handed and the threads formed on the inner component 504 can be left-handed). In such a configuration, a single turn of the actuator 506 can translate the inner component 504 with respect to the outer component by twice the pitch of the threads. In addition, the threads formed on the various surfaces of the screw extension instrument 500 can be square or buttress threads (i.e., having a square or partially-square cross-sectional profile), as these profiles can maximize the transmission of force between the components along the longitudinal axis of the instrument 500.

In addition, the proximal end of the inner component can include a stop 708 to prevent the inner component from retracting too far into the actuator 506 as it is rotated. Still further, the inner component can include one or more protrusions 710 or other features formed on an outer surface thereof. The one or more protrusions 710 can be configured to interface with one or more features of the outer component 502, such as the opposed slots 622, to prevent the inner component from rotating with respect to the outer component as it translates longitudinally. In other embodiments, however, the orientation of these features can be reversed. For example, a protrusion, pin, set screw, or other feature can be formed on an inner surface of the outer component 502 and a slot or other complementary recess can be formed on an outer surface of the inner component 504. Regardless of the orientation, the interaction of a protruding feature and a complementary slot or recess can prevent undesired rotation of the inner component relative to the outer component.

The inner component 504 can have a constant outer diameter, as shown in FIG. 7, or it can include portions having different diameters, as shown in FIG. 5. For example, in an embodiment in which the outer diameter of a proximal portion of the inner component 504 is larger than a diameter of the first bore 116, a distal portion 514 of the inner component 504 can have a reduced diameter such that the inner component can fit within the recess 114 of the receiving member 108. The reduced diameter portion 514 can extend for any desired length toward the proximal end of the inner component 104 (up to and including the entire length of the inner component, as shown in FIG. 7). In embodiments in which receiving members with extending tabs (e.g., tabs 404A, 404B shown in FIG. 4) are utilized, the reduced diameter portion 514 can extend for at least the length of the extending tabs (thus, the extending tabs would be accommodated in the space visible between the reduced diameter portion 514 and the outer component 502 in FIG. 5).

Moreover, in some embodiments, the inner component 504 can also include an inner lumen 516 extending therethrough. The inner lumen 516 can allow additional instruments to be inserted therethrough to access the polyaxial screw 100. Exemplary instruments can include a rod pusher that can be used to press a spinal fixation rod into the receiving member 108, or a bone anchor driver that can be used to implant the bone anchor 102 into a vertebra.

Figure 8:
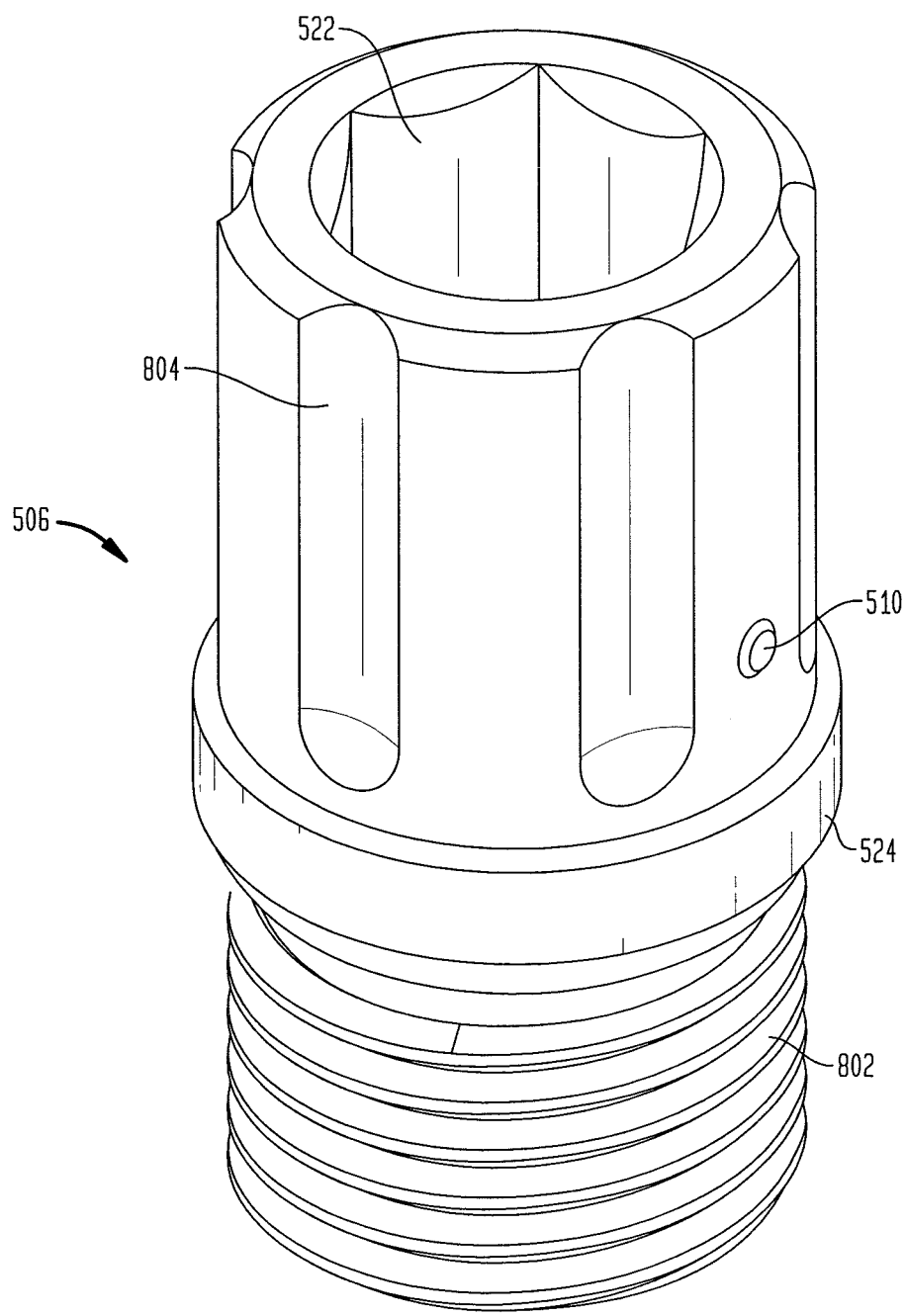
FIG. 8 is a perspective view of an actuator of the screw extension instrument of FIG. 5.

FIG. 8 illustrates one embodiment of the actuator 506 of the screw extension instrument 500. The actuator 506 can have a variety of shapes and sizes. In one embodiment, the actuator 506 has a generally cylindrical shape and is configured to be threadably mated with the outer component 502 from the proximal end of the outer component. The actuator 506 therefore includes a threaded outer surface 802 at a distal end thereof. The actuator 506 can also include an inner lumen 518 extending therethrough that can communicate with the inner lumen 516 of the inner component 504, thereby allowing other tools or instruments to be passed through the screw extension instrument 500 down to the polyaxial screw 100. A distal portion 520 of the inner lumen 518 of the actuator can include threads that are opposite-handed of the threaded outer surface 802. The threads can be configured to interface with the threaded outer surface 706 of the inner component 504. A proximal portion 522 of the inner lumen 518 can have a cross-sectional profile configured to interface with a driver or other tool that can be used to rotate the actuator. In addition, an outer surface of the actuator 506 can include gripping features 804 along a proximal portion thereof to allow for hand manipulation if a driver or other tool is not used.

The actuator can also include a stopping pin or protrusion 510 mounted in a sidewall thereof and extending into the inner lumen 518. The stopping pin 510 can be configured to abut against the stop 708 formed on the proximal end of the inner component 504, thereby preventing the inner component from being retracted too far into the inner lumen 518 of the actuator 506 during operation.

Furthermore, the actuator can include an enlarged diameter portion 524 formed along a portion thereof proximal to the threaded outer surface 802. The enlarged diameter portion 524 can extend toward the proximal end of the actuator by any length, and may extend to the proximal end of the actuator, resulting in an actuator having a single diameter proximal of the threaded outer surface 802. The enlarged diameter portion 524 can be configured to abut against an inner surface of the tabs 607A, 607B of the outer component 502, preventing the tabs from being pinched together. This can aid in securing the connection between the opposed arms 608A, 608B and the receiving member 108, as the tabs 607A, 607B must be pinched together in order to separate the opposed arms 608A, 608B and release the receiving member 108. The actuator 506, in combination with the retaining ring 508, can provide a very secure connection between the screw extension instrument and the polyaxial screw. The rigidity and support provided by the screw extension instrument 500 can allow a surgeon or other user to directly manipulate the outer component in order to adjust the position and/or orientation of the vertebra coupled to the screw. This can in some embodiments eliminate the need for additional facilitators or other instruments to aid in manipulation of the vertebra.

Referring back to FIG. 5, the operation of the screw extension instrument 500 can be explained in more detail. To begin, the outer component 502 can be separated from the inner component 504 and the actuator 506. This can be done, for example, by rotating the actuator 506 in a counter-clockwise direction until the threaded outer surface 802 of the actuator 506 disengages from the threads 512 formed on the inner surface of the outer component 502. Given the opposite-handed threads formed on the outer and inner surfaces of the actuator 506, in combination with the protrusion 710 that prevents rotation of the inner component 504, the counter-clockwise rotation will cause the inner component 504 to retract into the inner lumen 518 of the actuator 506. Once the threaded outer surface 802 disengages from the outer component 502, the inner component 504 and actuator 506 can be withdrawn from the proximal end of the outer component 502.

The opposed tabs 607A, 607B at the proximal end of the outer component 502 can then be compressed together to draw the opposed arms 608A, 608B apart at the distal end of the outer component. The receiving member 108 of the polyaxial screw 100 can be placed between the opposed arms 608A, 608B such that the opposed slots 609A, 609B align with the opposed U-shaped slots that extend between the opposed legs 124A, 124B of the receiving member. The opposed tabs 607A, 607B can be released, allowing the bias from the connecting portions 604A, 604B to draw the opposed arms 608A, 608B together and grasp the receiving member 108 therebetween.

The inner component 504 and actuator 506 can then be inserted into the outer component 502 from a proximal end thereof. The protrusion 710 of the inner component can be aligned with the slot 622 of the outer component, which will also align the opposed slots 704A, 704B formed between the opposed arms 702A, 702B of the inner component 504 with the opposed slots 609A, 609B of the outer component 502 and those of the receiving member 108. The actuator 506 can be rotated clockwise to engage the threaded outer surface 802 of the actuator 506 with the threads 512 formed on the inner surface of the outer component 502. The clockwise rotation that advances the actuator 506 distally relative to the outer component also causes the inner component 504 to advance distally out of the actuator due to the opposite-handed threads and the protrusion 710 that prevents the inner component from rotating. Furthermore, as the actuator is advanced distally into the outer component 502, the enlarged diameter portion 524 of the actuator presses against the inner surfaces of the opposed tabs 607A, 607B, urging the tabs away from one another and securing the coupling at the distal end between the receiving member 108 and the opposed arms 608A, 608B.

The actuator 506 can continue to be rotated clockwise to further distally translate the inner component 504 relative to the outer component 502. The opposed arms 702A, 702B at the distal end of the inner component 504 can contact an upper surface of a compression member disposed in a distal portion of the receiving member 108 and apply a distal force thereto. The distal force can move the compression member from a first position in which the threaded shank of the polyaxial screw 100 is polyaxially movable relative to the receiving member to a second position in which the orientation of the threaded shank and the receiving member are locked.

With the polyaxial screw converted to a monoaxial configuration, a surgeon or other user can directly manipulate the screw extension instrument 500 to adjust the position and/or orientation of the vertebra in which the polyaxial screw is implanted. Directly manipulating the screw extension instrument can be advantageous because the larger instrument provides an easier device to grip, and because in certain procedures (e.g., MIS procedures), only the instrument may extend out of the patient's body above the patient's tissue and skin.

The polyaxial screw can be repeatedly converted between polyaxial and monoaxial configurations by rotating the actuator until the desired configuration is achieved, providing a surgeon or other user with a great deal of flexibility in rod capture, derotation, fracture closure, and many other spinal surgery procedures. In addition, in some embodiments additional tools can be introduced down the inner lumens of the actuator and inner component to the polyaxial screw. Additional details of an exemplary surgical procedure utilizing polyaxial screws and spinal fixation elements are provided in U.S. Pat. No. 7,666,188, the contents of which are hereby incorporated by reference in their entirety. When final positioning has been achieved, the inner component and actuator can be removed from the outer component as described above, and a conventional closure mechanism can be inserted to permanently lock the orientation of the polyaxial screw and secure the spinal fixation element within the receiving member.

Figure 9:
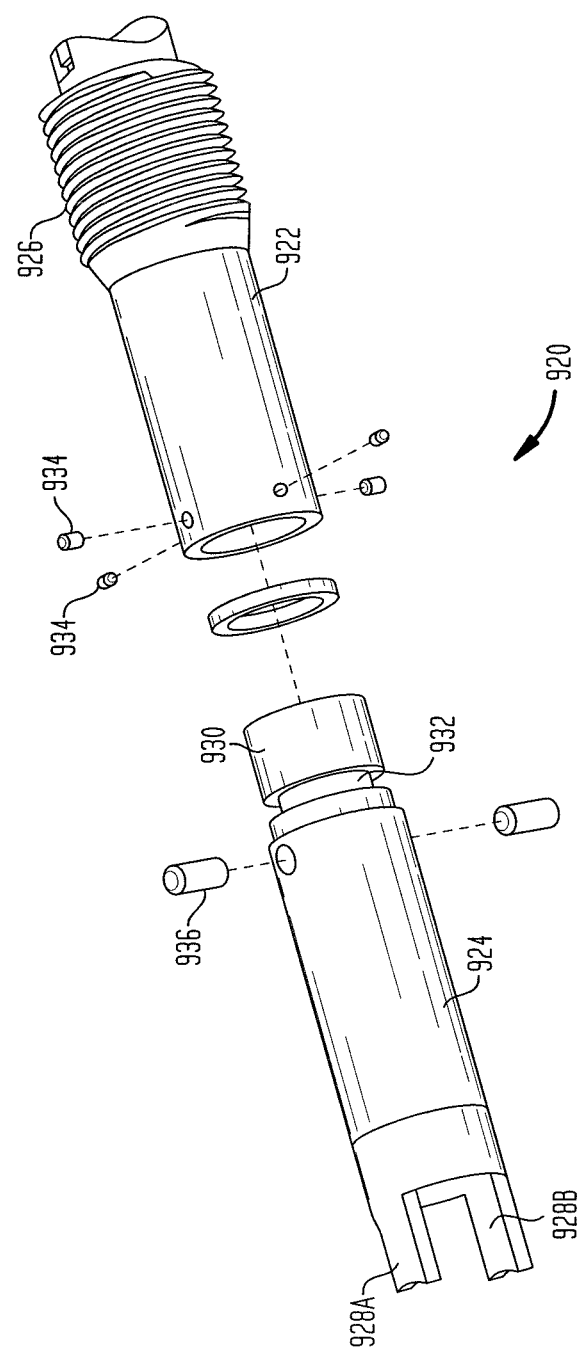
FIG. 9 is an exploded view of one embodiment of an inner component.

A number of variations of the embodiments shown in FIGS. 5-8 are possible, all of which are considered within the scope of the invention. For example, there are several different variations on the above-described embodiments that can be used to accomplish the desired longitudinal translation between the outer component 502 and the inner component 504. In one embodiment, the actuator can be eliminated entirely, thereby allowing an inner component to threadably engage directly with the outer component. FIG. 9 illustrates an exemplary embodiment of this type of inner component 920. The inner component 920 includes a proximal portion 922 and a distal portion 924. The proximal portion 922 can include threads 926 formed on an outer surface thereof and configured to interface with threads formed on an inner surface of an outer component, such as the threads 512. The proximal portion 922 can also include a handle formed at a proximal end thereof (not shown) to allow an operator to rotate the proximal portion 922 by hand. In another embodiment, a proximal-most surface of the proximal portion 922 can include a drive feature configured to mate with a drive tool that can be used to rotate the proximal portion 922.

The distal portion 924 can include opposed arms 928A, 928B that are similar to the opposed arms 702A, 702B discussed above. The proximal end of the distal portion 924, however, can be configured to rotatably couple to the distal end of the proximal portion 922. In particular, the proximal portion 922 can include an inner lumen formed in a distal end thereof, and the inner lumen can be configured to receive a proximal end 930 of the distal portion 922. The proximal end 930 of the distal portion 922 can further include a circumferential groove 932 formed therein that can be seated within the inner lumen of the proximal portion 922 when the two portions are coupled together. One or more set screws 934 can be inserted through a sidewall of the proximal portion 922 as shown in the figure such that they sit within the groove 932 of the distal portion and prevent the two portions from decoupling. In addition, the set screws can allow the two portions to rotate relative to one another. Moreover, the distal portion 924 can include one or more protrusions 936, similar to protrusions 710 discussed above, that can interface with a slot (e.g., slot 622) or other feature formed in an outer component to prevent the distal portion 924 from rotating relative to the outer component.

In another embodiment, the actuator 506 can be modified such that it does not include threads formed on a surface of the inner lumen 518. Similarly, the inner component 504 can be modified such that it does not include threads formed on the outer surface 706 thereof. As a result, the inner lumen 518 can slidably receive the outer surface 706 of the inner component. The inner component or inner lumen of the actuator can include a groove formed therein that can receive a set screw coupled to the other component, similar to the mechanism described above with respect to FIG. 9, to rotatably couple the actuator to the inner component. In other embodiments, a groove formed in the sidewall of one of the components can be used in conjunction with one or more resilient tabs that extend into the groove when the inner component is slidably mated to the actuator. As a result, the inner component can be rotatably mated to the actuator and the actuator can subsequently be threaded into the outer component as described above. The same protrusions 710 on the inner component can prevent it from rotating relative to the outer component as the actuator is rotated.

In still another embodiment, the actuator 506 and the outer component 502 described above can be modified such that the outer surface of the actuator does not have threads 802 formed thereon and the inner surface of the outer component similarly does not have threads 512 formed thereon. As a result, the actuator can be slidably received within the inner lumen 603 of the outer component until a portion of the actuator, e.g., the enlarged diameter portion 524, abuts against a shelf or other feature of the outer component. In such an embodiment, the actuator can rotate relative to the outer component without translating, and the inner component can translate without rotating due to the threaded coupling between the outer surface of the inner component and the inner lumen of the actuator in combination with the protrusions 710 and slots 622.

Furthermore, the outer component can include a feature, such as a set screw, pin, or other projection, that extends into a complementary feature, such as a groove formed around a circumference of the actuator, to prevent the actuator from being pushed proximally out of the outer component when, e.g., a distal force is applied to the compression member of a polyaxial screw by the inner component. In other embodiments, one or more resilient tabs can be configured to extend into a groove formed on either the outer component or actuator to provide the same functionality. One of ordinary skill in the art will appreciate that a number of other retention mechanisms can also be employed for this purpose.

In addition to variations of the actuator, the outer component 502 described above is one of a number of possible outer components that can be configured to releasably couple to a receiving member of a polyaxial screw. A number of additional mechanisms for releasably coupling with a polyaxial screw are described below and further explained in U.S. Pat. Nos. 7,179,261, 7,918,857, and 7,918,858, the contents of which are hereby incorporated by reference in their entirety.

Figure 10A:
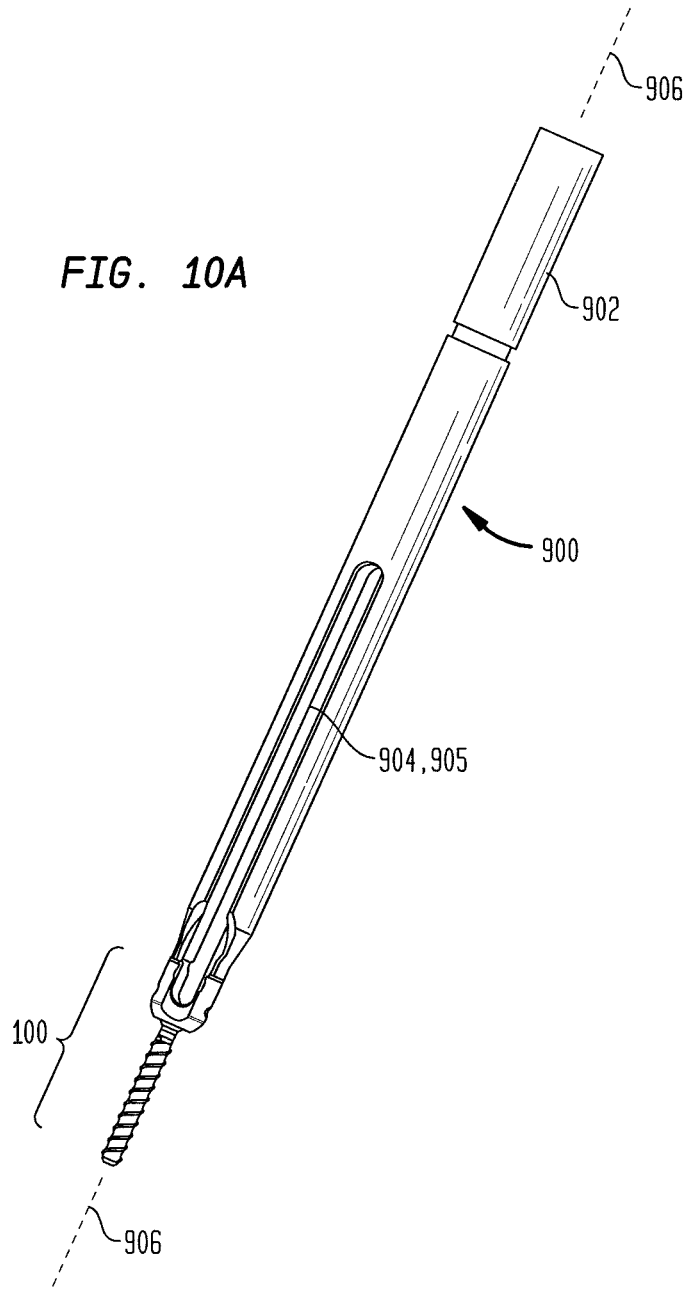
FIG. 10A is a perspective view of an alternative embodiment of a screw extension instrument.

FIGS. 10A-12 illustrate another embodiment of a screw extension instrument utilizing an alternative mechanism for engaging a receiving member of a screw. With reference to FIGS. 10A and 10B, an outer component 900 is shown that includes an inner tube 1002 and an outer tube 1004 disposed about at least a portion of the inner tube 1002. In the illustrated embodiment, the outer tube 1004 is coaxially disposed about the inner tube 1002 such that the inner tube 1002 and the outer tube 1004 share a common longitudinal axis 906. One skilled in the art will appreciate, however, that the outer tube 1004 and inner tube 1002 need not be coaxially aligned. The inner tube 1002 and the outer tube 1004, in the exemplary embodiment, are generally cylindrical in shape, having an approximately circular cross-section. One skilled in the art will appreciate, however, the inner tube 1002 and the outer tube 1004 may have other cross-sectional shapes, including, for example, elliptical or rectilinear. In the exemplary embodiment, the inner tube 1002 and outer tube 1004 have analogous cross-sections, however, one skilled in the art will appreciate the inner tube 1002 and the outer tube 1004 can have different cross-sectional shapes. The axial length of the inner tube 1002 and outer tube 1004 may vary depending on, for example, the patient anatomy, the procedures employed, etc.

Figure 10B:
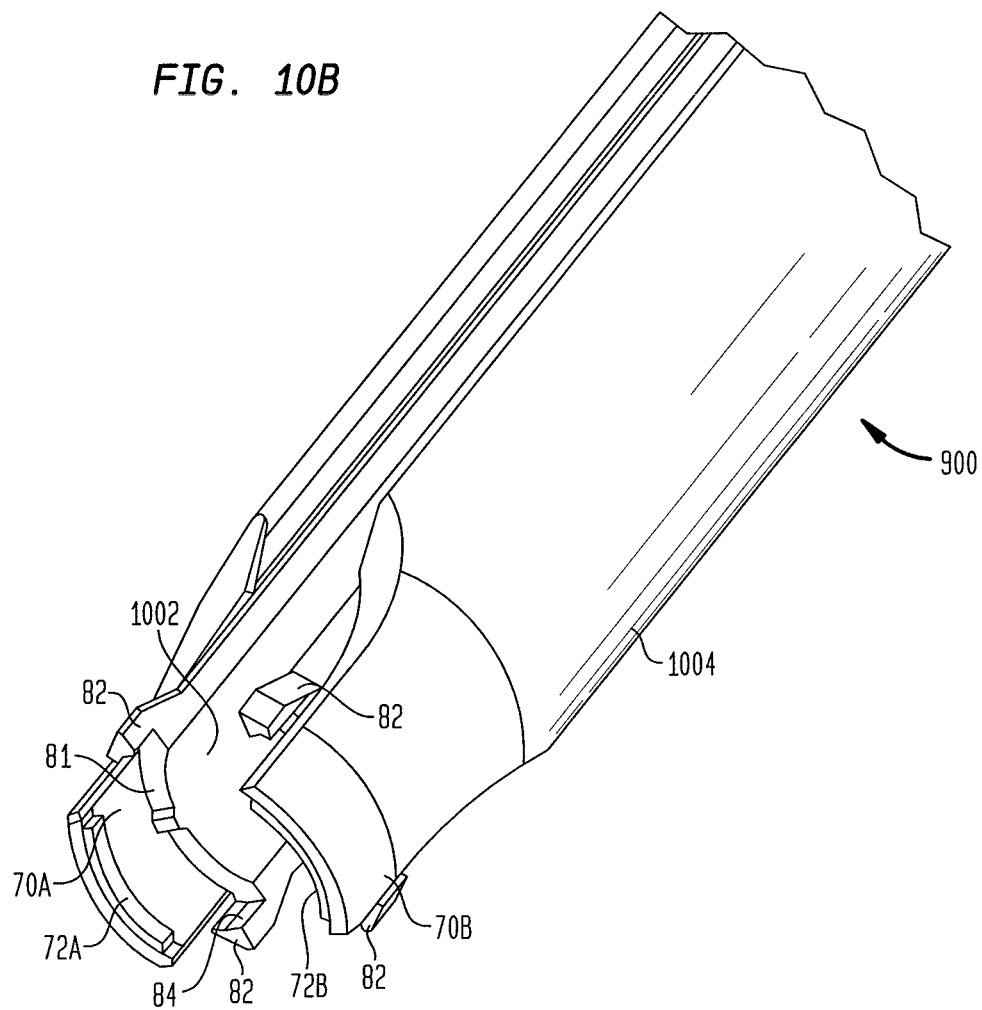
FIG. 10B is a perspective view of a distal end of the device shown in FIG. 10A.

The inner tube or sleeve 1002 includes a proximal and a distal end, and has an inner lumen extending between the proximal and distal ends. The outer tube or sleeve 1004 similarly includes a proximal end and a distal end, and has an inner lumen extending between the proximal and distal ends. The inner tube 1002 can be positionable within the inner lumen of the outer tube 1004. Furthermore, the inner tube 1002 can be longitudinally adjustable with respect to the outer tube 1004. For example, the inner tube 1002 may adjustable from a first, proximal position, in which the distal end of the inner tube 1002 is positioned proximal to the distal end of the outer tube 1004 as illustrated in FIG. 10B, and a second, distal position, in which the distal end of the inner tube 1002 is positioned proximate to the distal end of the outer tube 1004 (i.e., the inner tube 1002 is translated distally from the position shown in FIG. 10B toward the distal end of the outer tube 1004). In the exemplary embodiment, the distal end of the inner tube 1002 preferably contacts at least a portion of the polyaxial screw 100 when the inner tube 1002 is in the second position.

In order to effect the relative movement of the inner tube 1002 and the outer tube 1004, the outer component 900 may include an adjustment mechanism 902 that allows an operator to adjust the relative longitudinal position of the inner tube 1002 and the outer tube 1004. In the illustrated embodiment, for example, the adjustment mechanism 902 is a hollow, tubular shaped cap having internal threads that engage external threads provided on the proximal end of the outer tube 1004. The threads allow the cap to be longitudinally adjusted relative to the outer tube 1004 independently of any adjustment of the inner component relative to the outer component, as described above. In the exemplary embodiment, the inner tube 1002 can be connected to the cap and, thus, can move with cap as the cap is advanced or withdrawn relative to the outer tube 1004.

Similar to the screw extension instrument 500 discussed above, the inner tube 1002 may have one or more sidewall openings or slots 904 formed therein. In the illustrated exemplary embodiment, the inner tube 1002 includes opposed slots 904 that extend longitudinally from the distal end of the inner tube 1002. Like the inner tube 1002, the outer tube 1004 may have one or more sidewall openings or slots 905 formed therein. In the illustrated exemplary embodiment, the outer tube 1004 includes opposed slots 905 that extend longitudinally from the distal end of the outer tube 1004. The slots 904 and 905 can be used to facilitate positioning of a spinal fixation element, such as a rod or a plate, relative to one or more bone anchors. To facilitate positioning of a spinal fixation element, the slots 904, 905 are preferably aligned with one another along at least a portion of the longitudinal axis of the outer component 900. The width and length of the slots 904, 905 may be varied depending on the particular methods, instruments, and fixation elements being employed. In one exemplary embodiment, for example, the length of the slots 904, 905 is selected to span at least from the skin incision to the distal end of the inner tube 1002 and the outer tube 1004, respectively. In such embodiments, the slots 904, 905 may be accessible from outside of the patient. In another exemplary embodiment, the length of the slots 904, 905 is selected to span from the distal end of the inner tube 1002 and the outer tube 1004, respectively, to a point distal to the skin incision. In such embodiments, the slots 904, 905 may be accessible only from the inner lumens of the inner and outer tubes.

In embodiments in which multiple slots are employed, the slots 904, 905 need not be similarly sized (width and/or length). For example, the one or more of the slots 904 may be sized differently than the one or more slots 905, the one or more of the slots 904 on the inner tube may be sized differently than other slots 904, and/or one or more of the slots 905 on the outer tube may be sized differently than other slots 905. Although the exemplary embodiment includes two opposing slots on the inner tube 1002 and the outer tube 1004, respectively, one skilled in the art will appreciate that any number of slots may be provided, e.g., no slots, one, two, three, etc. slots, may be provided depending on the method, instruments, and/or fixation element employed.

The distal end of the outer tube 1004 includes a pair of opposed longitudinally extending tabs 70A and 70B that may releasably engage a bone anchor. In the exemplary embodiment, the tabs 70A and 70B are defined by the sidewalls of the outer tube 1004 and are separated by slots 905. In certain exemplary embodiments, the tabs 70A and 70B may be flexible and resilient in the radial direction to facilitate connection to a bone anchor. For example, the tabs 70A and 70B may be flexed apart in the radial direction from a first, relaxed position to facilitate advancement of the tabs longitudinally over a portion of the bone anchor. Once positioned about a portion of the bone anchor, the tabs 70A and 70B may provide a radially compressive force on the bone anchor as the tabs 70A and 70B attempt to return to the first, relaxed position. In other exemplary embodiments, the tabs 70A and 70B need not be flexible and resilient.

Each tab 70A and 70B can include one or more radially inward facing projections 72 that are sized and shaped to seat within an opening provided in a portion of the receiving member of the polyaxial screw. The size, shape and number of projections can be varied depending on, for example, the opening(s) provided on the receiving member and the type of connection desired. In the illustrated exemplary embodiment, for example, each projection 72A, 72B is generally arcuate in shape and has a cross section that is complementary to an arcuate groove 130 provided in the receiving member 108 of the exemplary polyaxial screw 100 described above.

The distal end of the inner tube 1002 may include a contact surface 81 that contacts at least a portion of the receiving member when the inner tube 1002 is in the second position. In the illustrated exemplary embodiment, for example, the distal end of the inner tube 1002 may have two opposing generally arcuate contact surfaces 81. The contact surfaces 81, in the exemplary embodiment, are oriented approximately perpendicular to the longitudinal axis of the inner tube 1002. In the illustrated exemplary embodiment, the contact surfaces 81 are configured to contact a generally arcuate contact surface provided on the proximal end of the receiving member 108 of the exemplary polyaxial screw 100. Preferably, the contact surface 81 is complementary in size, shape, and orientation to the contact surface on the bone anchor. One skilled in the art will appreciate that the configuration of the contact surface 81, e.g., number, size, shape, and orientation of the contact surface 81, may be varied to, for example, suit the bone anchor being employed.

The distal end of the inner tube 1002 and/or the distal end of the outer tube 1004 may be configured to inhibit rotation of the receiving member relative to the outer component 900. For example, the distal end of the inner tube may include one or more finger-like extensions 82 that extend approximately axially from the distal end of the inner tuber 1002 and engage a bone anchor to inhibit rotation of the bone anchor relative to the outer component 900. For example, one or more of the extensions 82 may seat within a groove, recess, slot, or similar structure provided in the bone anchor. Alternatively, one or more of the extensions 82 may include a contact surface 84 for contacting an axially extending surface 152 of the receiving member.

The outer component 900 illustrated in FIGS. 10A and 10B can be used in conjunction with the inner component 504 described above to provide a screw extension instrument that can selectively and intraoperatively convert a polyaxial screw into a monoaxial screw while allowing for the passage of a rod or other spinal fixation element through the receiving member of the screw. In particular, an inner surface of the inner tube or sleeve 1002 can include threads designed to engage with the outer threaded surface 802 of the actuator 506, thereby providing longitudinal translation between the inner component and the outer component 900. The projection 710 of the inner component 504 can be configured to slide within the slot 904 to prevent the inner component from rotating with respect to the inner tube or sleeve 1002 of the outer component 900.

Figure 11:
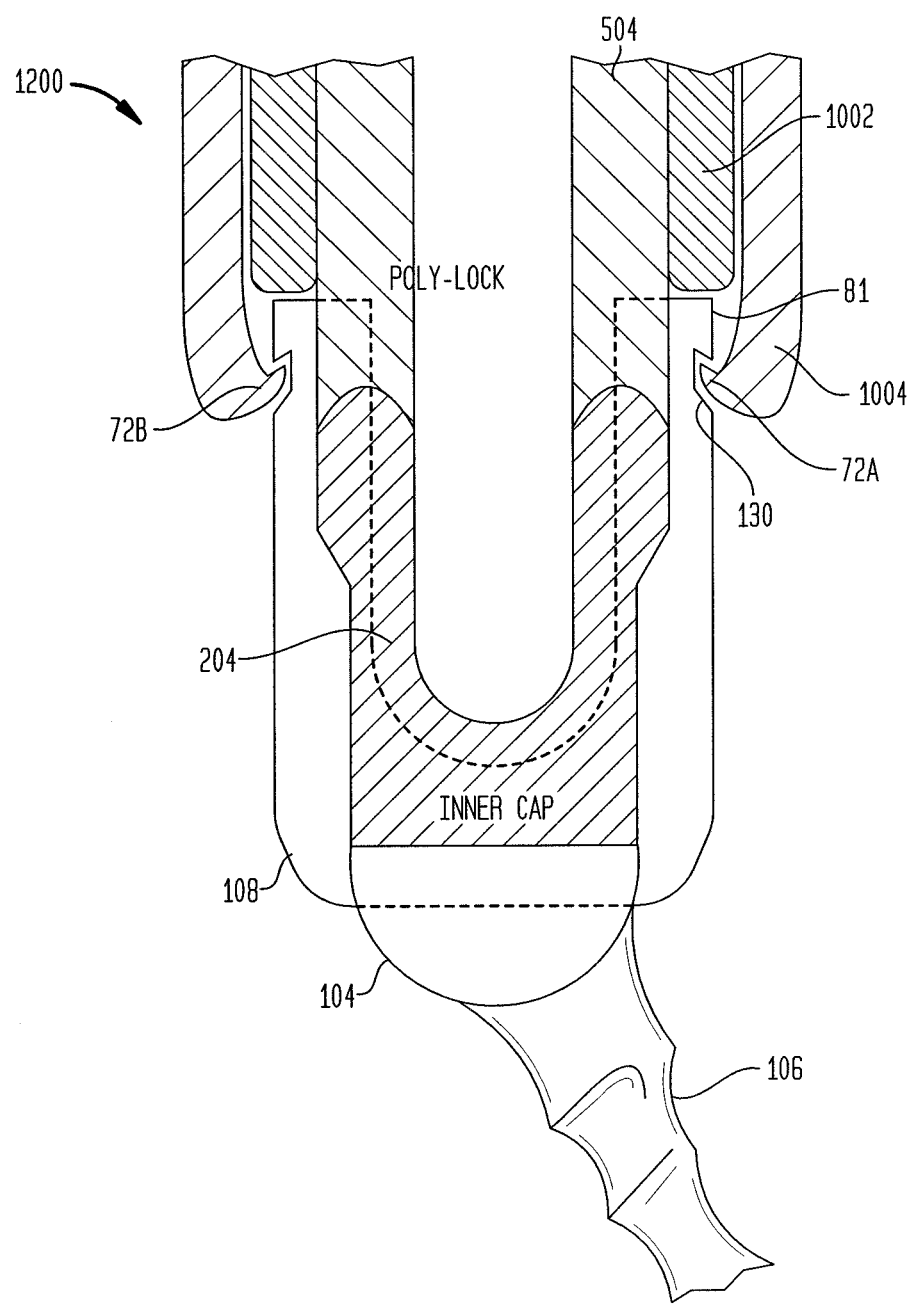
FIG. 11 is a front cross-sectional view of the distal end of the device shown in FIG. 9.

FIG. 11 schematically illustrates the operation of a screw extension device 1200 that includes the outer component 900 and inner component 504. Shown in cross-section is the polyaxial screw 100 including threaded shank 106, head 104, receiving member 108, and compression member 204. Also shown is the outer component 900 securely and releasably coupled to the receiving member 108. In particular, the outer tube or sleeve 1004 of the outer component 900 is extended over the outer surface of the receiving member 108 and projections 72A, 72B are engaged with the groove 130 formed in the receiving member 108. In addition, the inner tube or sleeve 1002 of the outer component has been translated to the second position described above in which the contacting surface 81 of the inner tube 1002 contacts an upper surface of the receiving member 108 to lock the connection between the outer tube 1004 and the receiving member 108.

Also visible in the figure is the inner component 504 extending beyond the distal end of the outer component 900 into the recess of the receiving member 108. As described above, a distal surface of the inner component 504 is in contact with an upper surface of the compression member 204 and can apply a distal force to the compression member to press it into the head 104 and lock the orientation of the threaded shank 106 relative to the receiving member 108.

Figure 12A:
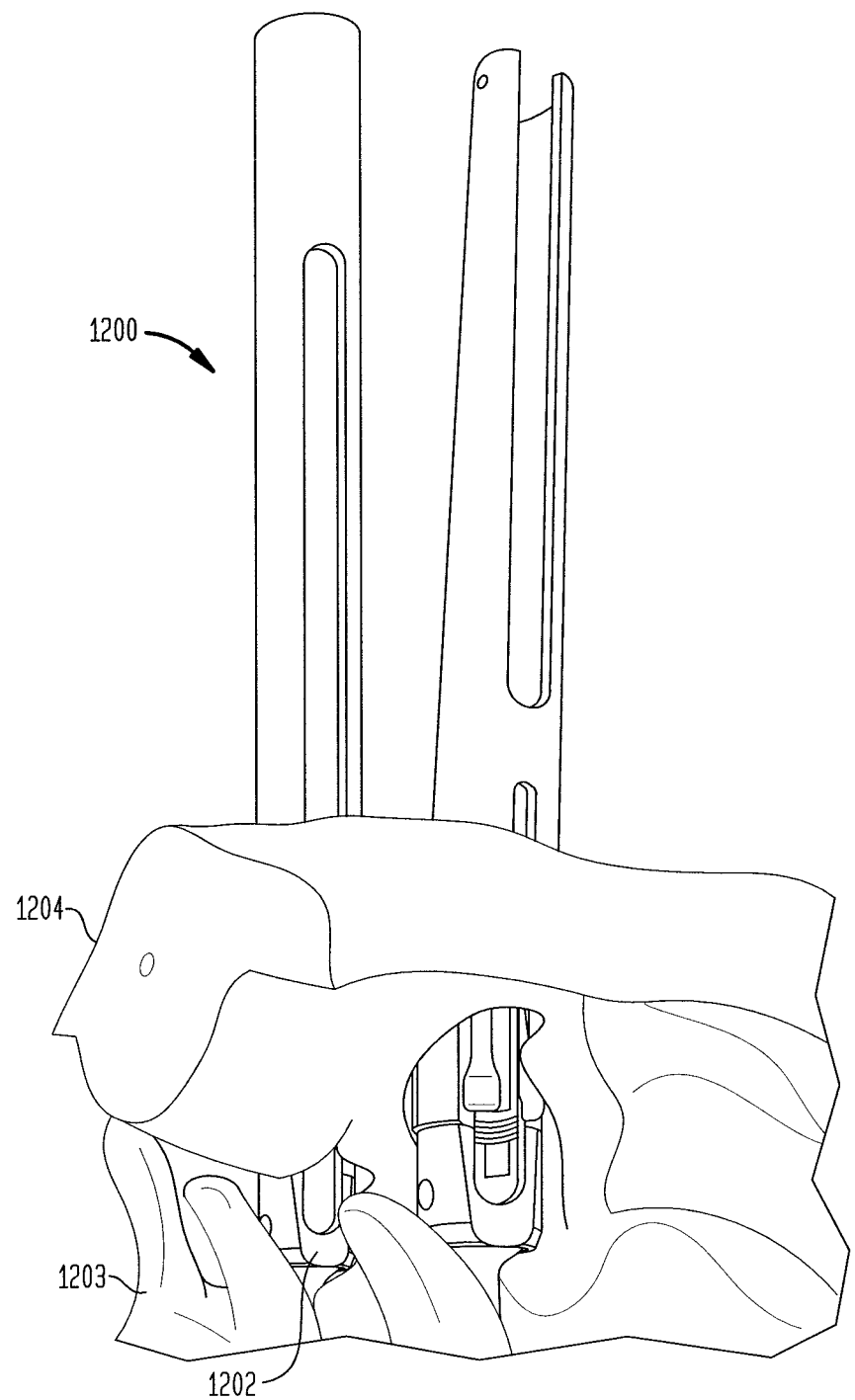
FIG. 12A is a perspective view of an implanted polyaxial screw attached to a screw extension instrument.
Figure 12B:
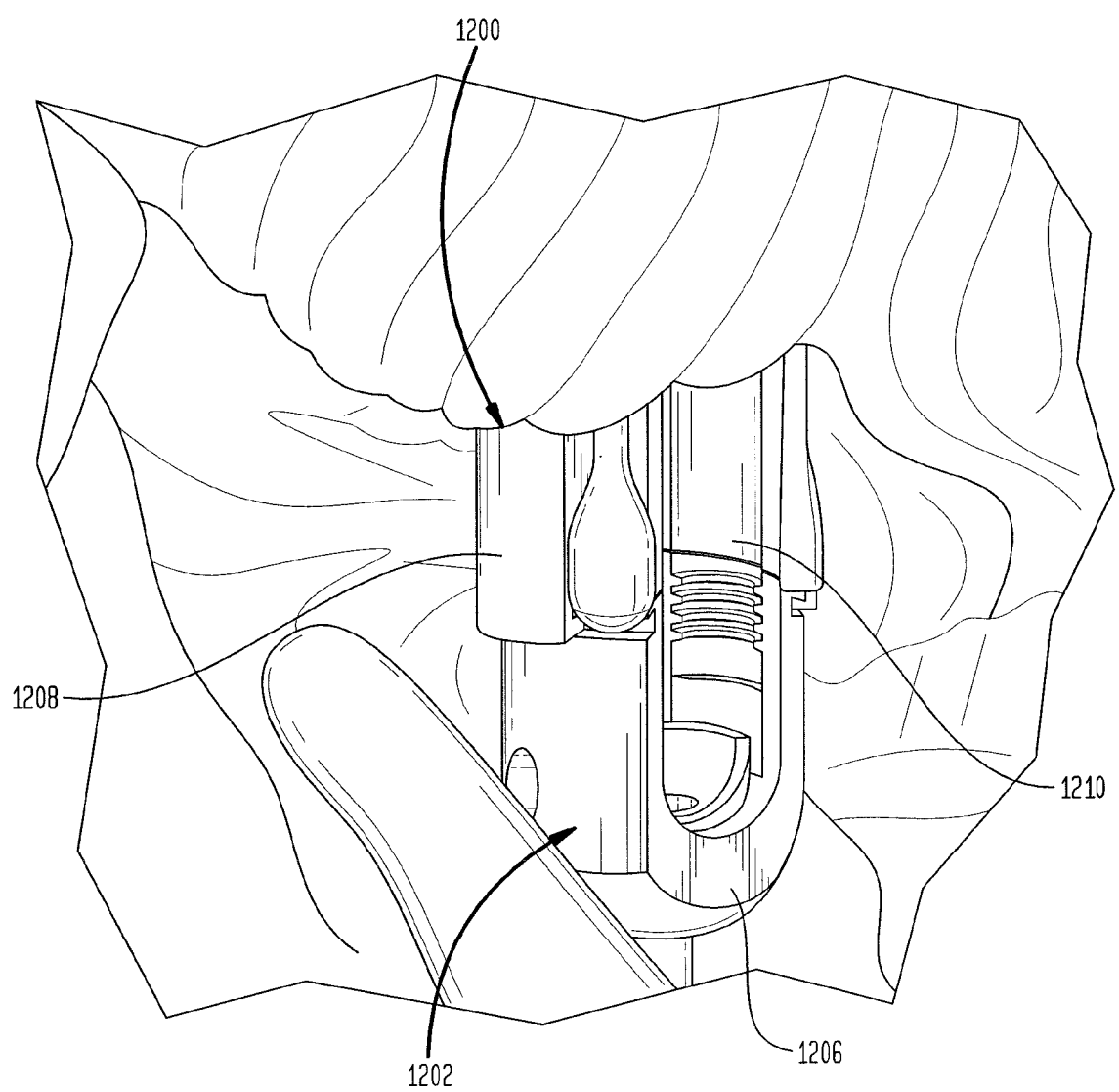
FIG. 12B is a close perspective view of the polyaxial screw of FIG. 10A showing the outer component coupled to the polyaxial screw.
Figure 12C:
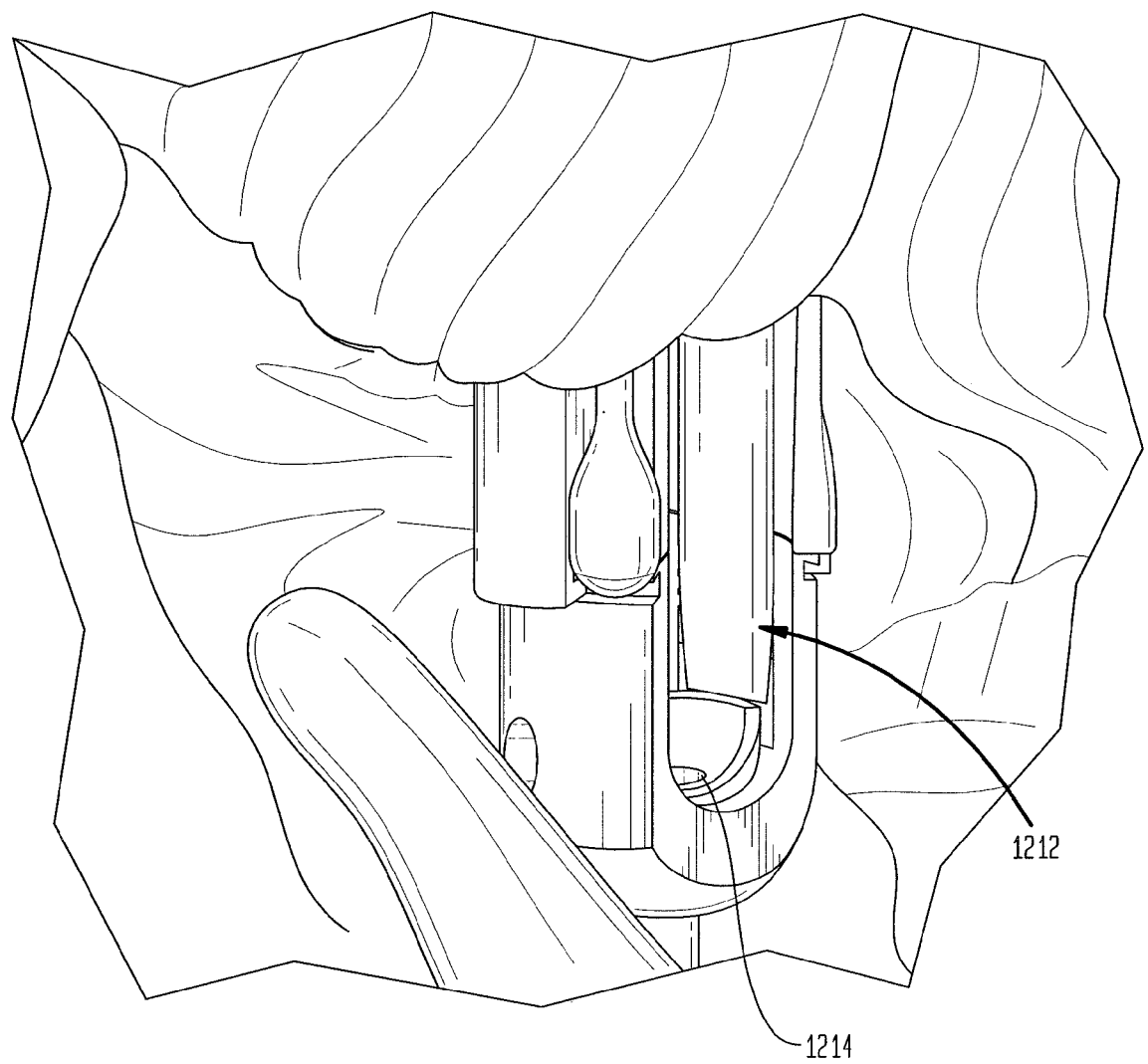
FIG. 12C is a close perspective view of the polyaxial screw of FIG. 10A showing the inner component translated distally to convert the polyaxial screw into a monoaxial screw.

FIGS. 12A-12C illustrate the screw extension instrument 1200 of FIG. 11 attached to a polyaxial screw 1202 implanted in a vertebra 1203. The screw extension instrument 1200 is shown extending through the muscle and tissue 1204 that lies above the vertebra, as would be the case in an MIS procedure. A second polyaxial screw attached to a screw extension device is also visible implanted in an adjacent vertebra.

The close perspective view of FIG. 12B illustrates the connection between the screw extension instrument 1200 and a receiving member 1206 of the polyaxial screw 1202. In particular, an outer tube or sleeve 1208 of an outer component of the instrument 1200 is disposed over a portion of an outer surface of the receiving member 1206, and an inner tube or sleeve 1210 of the outer component of the instrument has been advanced toward a distal end of the outer tube 1208 to abut against an upper surface of the receiving member 1206. The inner component of the screw extension instrument is not visible in this figure. FIG. 12C, in contrast, illustrates the screw extension instrument 1200 with the inner component 1212 advanced distally to apply a distal force to the compression member 1214 of the polyaxial screw 1202 and thereby convert the polyaxial screw into a monoaxial screw. In this configuration, a surgeon or other user can manipulate the proximal end of the screw extension instrument 1200 (see FIG. 12A) to adjust the position and/or orientation of the vertebra in which the polyaxial screw 1202 is implanted. In addition, if desired, the surgeon or other user could subsequently retract the inner component 1212 proximally to convert the monoaxial screw back into a polyaxial screw. This process can be repeated as desired to switch between monoaxial and polyaxial configurations.

Figure 13A:
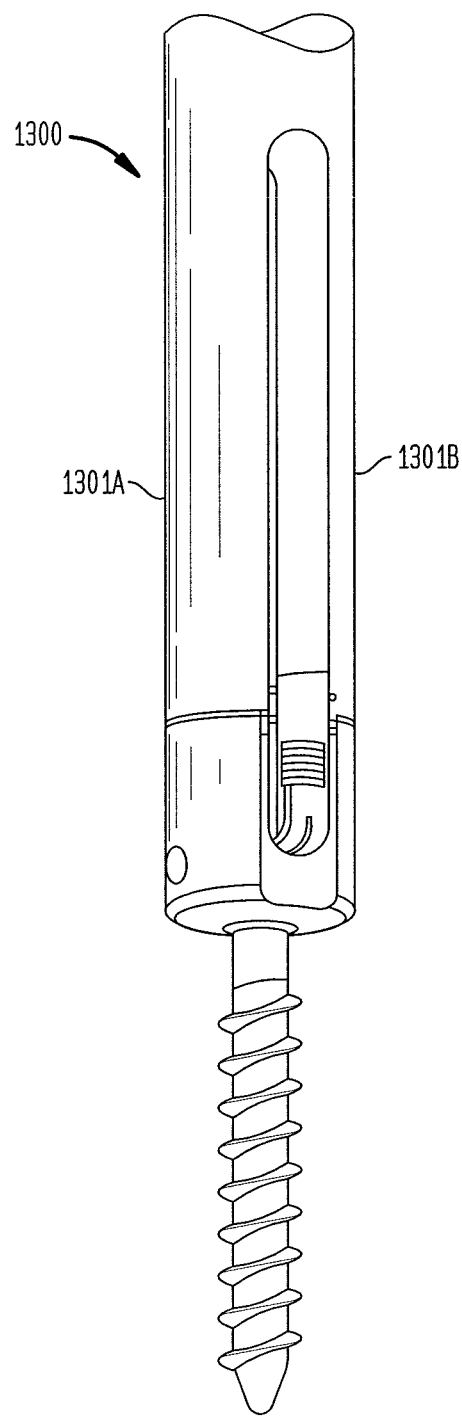
FIG. 13A is a perspective view of an alternative embodiment of an outer component of a screw extension instrument.
Figure 13B:
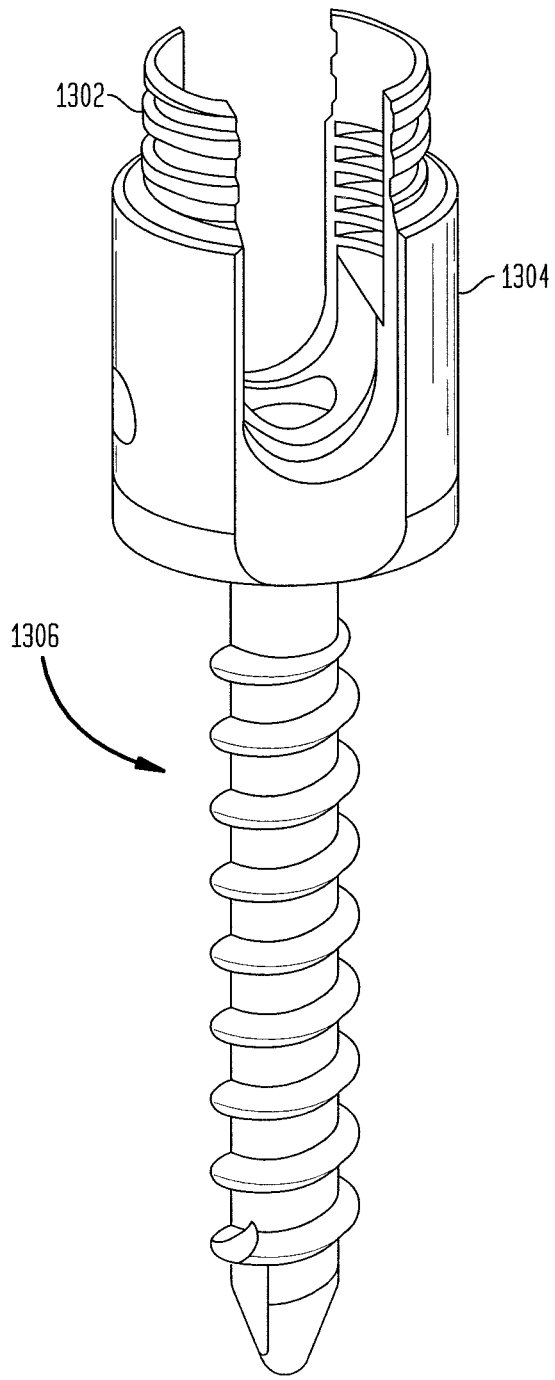
FIG. 13B is a perspective view of an alternative embodiment of a polyaxial screw configured for use with the screw extension instrument of FIG. 13A.

One skilled in the art will appreciate that the embodiments shown in FIGS. 5-12C are not the only possible mechanisms for releasably coupling an outer component of a screw extension instrument to a polyaxial screw. A number of other possible connection mechanisms are possible, including the threaded connection shown in FIGS. 13A-13B. In particular, an outer component 1300 can be provided having threads formed on an internal surface of opposed arms 1301A, 1301B at its distal end. These threads can engage with threads 1302 formed on an outer surface of a receiving member 1304 of a polyaxial screw 1306.

Figure 14A:
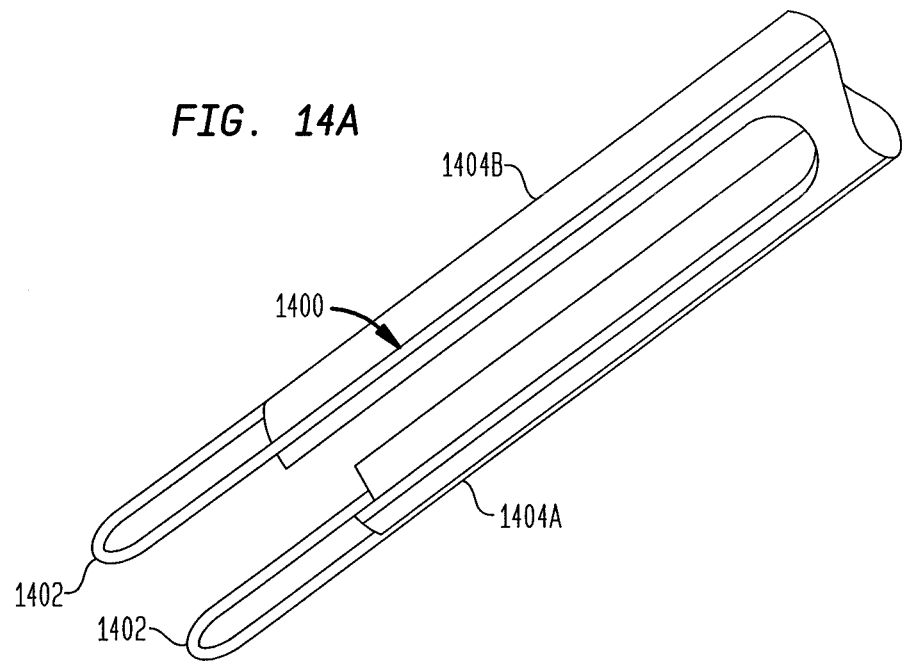
FIG. 14A is a perspective view of an alternative embodiment of an outer component of a screw extension instrument.
Figure 14B:
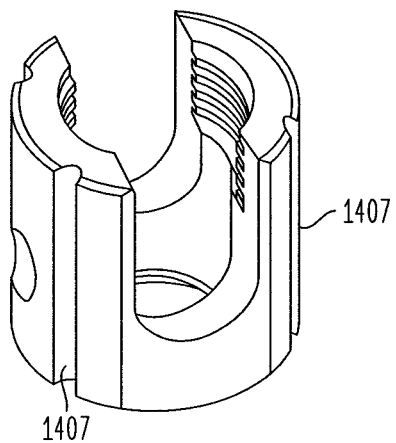
FIG. 14B is a perspective view of an alternative embodiment of a receiving member of a polyaxial screw configured for use with the screw extension instrument of FIG. 14A.
Figure 14C:
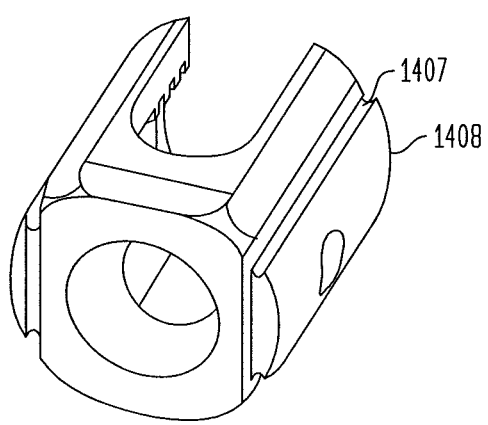
FIG. 14C is an alternative perspective view of the receiving member of FIG. 14B.

In another embodiment shown in FIGS. 14A-14C, wires 1402 extending down the opposed arms 1404A, 1404B of an outer component 1400 can be placed within grooves 1407 formed in a receiving member 1408 of a polyaxial screw. The wires 1402 can be retracted proximally to securely and releasably hold the receiving member 1408 in connection with the distal ends of the opposed arms 1404A, 1404B.

In addition, alternative embodiments of an inner component are also possible. For example, the opposite-handed threads disposed on the inner and outer surfaces of the actuator need not be present. Instead, an alternative embodiment can include a smooth-walled interface between the actuator 506 and inner component 504 with the use of a pin extending from a sidewall of one component into a groove formed in the other. In this manner, the actuator would still be free to rotate and engage the threads on the outer component, and the inner component would still translate without rotating relative to the outer component.

As has been described above, the various embodiments of a screw extension instrument described herein can be formed in a variety of sizes and shapes according to user desire, the type of procedure performed, the type of polyaxial screw used, etc. For example, the axial length of the outer component, inner component, and actuator can depend on patient anatomy, the procedures employed, and/or the area of the spine in which the instrument is employed. Furthermore, the instruments described herein can be constructed from any suitable biocompatible material, including, for example, a metal, such as stainless steel, or a polymer, and can be constructed using any conventional method of manufacturing medical devices.

The various embodiments of the devices described herein can be utilized in a variety of surgical procedures—both in the spine and elsewhere in the body. For example, the devices disclosed herein can be configured for use directly during an open surgical procedure, or they can be configured to be passed through one or more layers of tissue using one or more incisions during a minimally invasive surgical (MIS) procedure. Regardless of the type of operation, the instruments described herein can provide flexibility to surgeons by allowing for repeated and selective conversion of polyaxial screws to a monoaxial configuration without preventing the passage of a rod or other spinal fixation element through the polyaxial screw. In addition, the screw extension instrument provides a convenient and effective tool for surgeons to manipulate to adjust the position and/or orientation of a vertebra after a polyaxial screw has been converted to a monoaxial configuration.

In one embodiment, a method for correcting spinal deformities is provided that can include coupling a screw extension instrument to a receiving member of a polyaxial screw that is coupled to a threaded shank that is polyaxially movable relative to the receiving member. This can be accomplished using any of the various mechanisms described herein—or others known in the art—for coupling an instrument to a receiving head of a polyaxial screw. The method can further include advancing an inner component of the screw extension instrument relative to the receiving member of the polyaxial screw to cause the inner component to convert the polyaxial screw into a monoaxial screw. This can be accomplished, for example, by advancing the inner component to push on a compression member disposed within a distal portion of the receiving member of the polyaxial screw onto a head formed on the threaded shank of the polyaxial screw to thereby prevent movement of the head relative to the receiving member.

The method can include coupling the screw extension instrument to the receiving member of the polyaxial screw either before or after implanting the threaded shank of the polyaxial screw in a vertebra of a patient. In addition, the method can include passing a spinal fixation element, such as a spinal fixation rod, through the receiving member of the polyaxial screw after advancing the inner component of the screw extension instrument to convert the polyaxial screw into a monoaxial screw. This can be done, for example, when a surgeon or other user wishes to provisionally correct the position and/or orientation of a patient's vertebra before passing a rod through the implanted polyaxial screw or screws. To do so, the surgeon or other user can convert the polyaxial screw to a monoaxial screw using a screw extension instrument, manipulate the screw extension instrument to provisionally correct the vertebra, and then pass a spinal fixation element through the polyaxial screw.

Moreover, the method can also include retracting the inner component of the screw extension instrument relative to the receiving member to convert the monoaxial screw into a polyaxial screw. Indeed, the process of advancing and retracting the inner component of the screw extension instrument can be repeated as many times as desired to continually convert the polyaxial screw into a monoaxial configuration and vice versa. In some embodiments, for example, a surgeon or other user may retract the inner component to return the screw to a polyaxial configuration after provisionally correcting the vertebra's position but before passing a spinal fixation element through the receiving member of the screw. By converting the screw back to a polyaxial configuration before passing a spinal fixation element, the surgeon or other user can take advantage of the flexibility of polyaxial movement when passing the spinal fixation element.

Finally, the method can also include removing the inner component of the screw extension instrument and inserting a closure mechanism into the receiving member of the polyaxial screw. The closure mechanism can be used to permanently or temporarily fix the orientation of the receiving member relative to the threaded shank, as well as the position and/or orientation of the polyaxial screw relative to the spinal fixation element.

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention. For example, the screw extension instruments disclosed herein may be disassembled partially or completely. In particular, the outer component, inner component, and actuator, as well as any smaller components thereof, can be separated from one another.

Preferably, the devices described herein will be processed before surgery. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. In other embodiments, an instrument can be sterilized using any number of ways known to those skilled in the art including ethylene oxide, steam, autoclave, and a liquid bath (e.g., cold soak).

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:
1. A spinal screw extension instrument, comprising:
an outer component having an inner lumen extending therethrough and a distal end with opposed arms configured to engage a receiving member of a polyaxial screw such that opposed slots formed between the opposed arms overlap with opposed slots formed in the receiving member; and
an inner component disposed within the inner lumen of the outer component and having a distal end with opposed arms and opposed slots formed between the opposed arms, the inner component being configured to translate longitudinally relative to the outer component such that the opposed arms of the inner component overlap with the opposed arms of the outer component and the opposed slots of the inner component overlap with the opposed slots of the outer component and the receiving member, the opposed arms of the inner component being configured to apply a distal force to a compression member of the polyaxial screw disposed within a distal portion of the receiving member to thereby convert the polyaxial screw to a monoaxial screw;
wherein the outer component comprises an outer sleeve configured to engage a feature formed on an outer surface of the receiving member of the polyaxial screw and an inner sleeve disposed within the outer sleeve and configured to abut against an upper surface of the receiving member of the polyaxial screw.

2. The instrument of claim 1, wherein the distal end of the inner component extends distally beyond the distal end of the outer component when applying the distal force to the compression member of the polyaxial screw.

3. The instrument of claim 1, further comprising an actuator coupled to the outer component and the inner component and configured to effect the longitudinal translation of the inner component relative to the outer component.

4. The instrument of claim 3, wherein the actuator comprises a threaded outer surface configured to engage with a threaded surface of the inner lumen of the outer component, and an inner lumen having a threaded surface configured to engage with a threaded outer surface of the inner component.

5. The instrument of claim 1, wherein the outer component comprises opposed portions coupled such that the opposed arms at the distal end of the outer component are biased toward one another.

6. The instrument of claim 5, further comprising a retaining ring coupled to one of the opposed portions and encircling both opposed portions.

7. The instrument of claim 1, wherein the inner component includes a surface feature to prevent rotation relative to the outer component during longitudinal translation.

8. A spinal screw extension instrument, comprising:
an outer component having an outer sleeve configured to engage a feature formed on an outer surface of a receiving member of a polyaxial screw, an inner sleeve disposed within the outer sleeve and configured to abut against an upper surface of the receiving member of the polyaxial screw, and an inner lumen extending therethrough; and
an inner component disposed within the inner lumen of the outer component, the inner component being configured to translate distally relative to the outer component and apply a force to a compression member of the polyaxial screw disposed within the receiving member to prevent movement of the receiving member relative to a bone anchor of the polyaxial screw;
wherein, when the inner component is applying the force to the compression member, a spinal fixation rod can be passed through a recess formed in the receiving member.

9. The instrument of claim 8, wherein the inner component is configured to directly contact the compression member to apply the force thereto.

10. The instrument of claim 8, wherein a distal end of the inner component includes opposed arms configured to align with two legs of a U-shaped receiving member such that opposed slots between the opposed arms align with the recess disposed between the two legs of the receiving member.

11. The instrument of claim 8, further comprising an actuator coupled to the outer component and the inner component and configured to effect the translation of the inner component relative to the outer component.

12. The instrument of claim 11, wherein the actuator comprises a threaded outer surface configured to engage with a threaded surface of the inner lumen of the outer component, and an inner lumen having a threaded surface configured to engage with a threaded outer surface of the inner component.

13. The instrument of claim 8, wherein the inner component includes a surface feature to prevent rotation relative to the outer component during translation.

14. A spinal screw extension instrument, comprising:
an outer component having an inner lumen extending therethrough and a distal end with opposed arms configured to engage a receiving member of a polyaxial screw such that opposed slots formed between the opposed arms overlap with opposed slots formed in the receiving member;
an inner component disposed within the inner lumen of the outer component and having a distal end with opposed arms and opposed slots formed between the opposed arms, the inner component being configured to translate longitudinally relative to the outer component such that the opposed arms of the inner component overlap with the opposed arms of the outer component and the opposed slots of the inner component overlap with the opposed slots of the outer component and the receiving member, the opposed arms of the inner component being configured to apply a distal force to a compression member of the polyaxial screw disposed within a distal portion of the receiving member to thereby convert the polyaxial screw to a monoaxial screw; and
an actuator coupled to the outer component and the inner component and configured to effect the longitudinal translation of the inner component relative to the outer component, the actuator having a threaded outer surface configured to engage with a threaded surface of the inner lumen of the outer component, and an inner lumen having a threaded surface configured to engage with a threaded outer surface of the inner component.

15. A spinal screw extension instrument, comprising:
an outer component comprising opposed portions having an inner lumen extending therethrough and a distal end with opposed arms configured to engage a receiving member of a polyaxial screw such that opposed slots formed between the opposed arms overlap with opposed slots formed in the receiving member, the opposed portions being coupled such that the opposed arms at the distal end of the outer component are biased toward one another;
a retaining ring coupled to one of the opposed portions and encircling both opposed portions; and
an inner component disposed within the inner lumen of the outer component and having a distal end with opposed arms and opposed slots formed between the opposed arms, the inner component being configured to translate longitudinally relative to the outer component such that the opposed arms of the inner component overlap with the opposed arms of the outer component and the opposed slots of the inner component overlap with the opposed slots of the outer component and the receiving member, the opposed arms of the inner component being configured to apply a distal force to a compression member of the polyaxial screw disposed within a distal portion of the receiving member to thereby convert the polyaxial screw to a monoaxial screw.

16. A spinal screw extension instrument, comprising:
an outer component having an inner lumen extending therethrough and a distal end configured to engage a receiving member of a polyaxial screw;
an inner component disposed within the inner lumen of the outer component, the inner component being configured to translate distally relative to the outer component and apply a force to a compression member of the polyaxial screw disposed within the receiving member to prevent movement of the receiving member relative to a bone anchor of the polyaxial screw; and
an actuator coupled to the outer component and the inner component and configured to effect the translation of the inner component relative to the outer component, the actuator having a threaded outer surface configured to engage with a threaded surface of the inner lumen of the outer component, and an inner lumen having a threaded surface configured to engage with a threaded outer surface of the inner component;

wherein, when the inner component is applying the force to the compression member, a spinal fixation rod can be passed through a recess formed in the receiving member.

* * * * *